US011061005B2

(12) United States Patent
Adam et al.

(10) Patent No.: US 11,061,005 B2
(45) Date of Patent: Jul. 13, 2021

(54) MASS SPECTROMETRY ASSAY METHOD FOR DETECTION AND QUANTITATION OF ORGANIC ACID METABOLITES

(71) Applicant: Metabolon, Inc., Morrisville, NC (US)

(72) Inventors: Klaus Peter Adam, Cary, NC (US); Andrew James Thompson, Raleigh, NC (US)

(73) Assignee: Metabolon, Inc., Morrisville, NC (US)

( * ) Notice: Subject to any disclaimer, the term of this patent is extended or adjusted under 35 U.S.C. 154(b) by 18 days.

(21) Appl. No.: 16/604,357

(22) PCT Filed: Apr. 16, 2018

(86) PCT No.: PCT/US2018/027734
§ 371 (c)(1),
(2) Date: Oct. 10, 2019

(87) PCT Pub. No.: WO2018/194958
PCT Pub. Date: Oct. 25, 2018

(65) Prior Publication Data
US 2020/0158702 A1 May 21, 2020

Related U.S. Application Data

(60) Provisional application No. 62/487,542, filed on Apr. 20, 2017.

(51) Int. Cl.
*G01N 27/622* (2021.01)
*H01J 49/16* (2006.01)
(Continued)

(52) U.S. Cl.
CPC ....... *G01N 30/7266* (2013.01); *G01N 27/622* (2013.01); *G01N 33/493* (2013.01);
(Continued)

(58) Field of Classification Search
CPC ............ G01N 30/7266; G01N 27/622; G01N 33/493; G01N 33/6848; G01N 2030/027; H01J 49/165
See application file for complete search history.

(56) References Cited

U.S. PATENT DOCUMENTS

2005/0070023 A1 3/2005 Nguyen et al.
2006/0160237 A1* 7/2006 Du .................... G01N 30/8675
436/129
(Continued)

OTHER PUBLICATIONS

Han et al. "An isotope-labeled chemical derivatization method for the quantitation of short-chain fatty acids in human feces by liquid chromatography-tandem mass spectrometry" Analytical Chemistry, 2015, 854 :85-94 (Year: 2015).*

(Continued)

*Primary Examiner* — David A Vanore
(74) *Attorney, Agent, or Firm* — NK Patent Law

(57) ABSTRACT

A method for determining in a sample, by mass spectrometry, the presence, absence, or amount of one or more analytes is described herein. The run time is less than six minutes. The method includes subjecting the sample to an ionization source under conditions suitable to produce one or more ions detectable by mass spectrometry from each of the one or more analytes, wherein the one or more analytes are derivatized prior to ionization; measuring, in a single injection, by mass spectrometry, the amount of the one or more ions from each of the one or more analytes; and using the measured amount of the one or more ions to determine the amount of each of the one or more analytes in the sample.

18 Claims, 10 Drawing Sheets

(51) Int. Cl.
G01N 30/72 (2006.01)
G01N 33/493 (2006.01)
G01N 33/68 (2006.01)
G01N 30/02 (2006.01)

(52) U.S. Cl.
CPC ........ *G01N 33/6848* (2013.01); *H01J 49/165* (2013.01); *G01N 2030/027* (2013.01)

(56) References Cited

U.S. PATENT DOCUMENTS

2016/0282351 A1 9/2016 Sugimoto et al.
2016/0341708 A1 11/2016 Zehentbauer

OTHER PUBLICATIONS

WIPO; International Preliminary Report on Patentability for International Patent Application No. PCT/US18/27734, dated Oct. 22, 2019, 12 pages.
ISA/US; International Search Report and Written Opinion for International Patent Application No. PCT/US18/27734 dated Jun. 19, 2018, 14 pages.
Han, J., et al. "An isotope-labeled chemical derivatization method for the quantitation of short-chain fatty acids in human feces by liquid chromatography-tandem mass spectrometry", ELSEVIER, Analytica Chimica Acta, Nov. 15, 2014, pp. 86-94.
Higashi, T., et al. "Simple and practical derivatization procedure for enhanced detection of carboxylic acids in liquid chromatography-electrospray ionization-tandem mass spectrometry", ELSEVIER, Journal of Pharmaceutical and Biomedical Analysis, Mar. 24, 2010, pp. 809-818.
Ambati Chandra, et al., "Identification and Quantitation of Malonic Acid Biomarkers of In-Born Error Metabolism by Targeted Metabolomics", J. Am. Soc. Mass Spectrom., 2017, vol. 28, 10 pages.
Stijntjes, Gerard J., et al., "High-performance liquid chromatography-fluorescence assay of pyruvic acid to determine cysteine conjugate beta-lyase activity: application to S-1,2-dichlorovinyl-L-cysteine and S-2-benzothiazolyl-L-cysteine", Anal Biochem., Nov. 1992, vol. 206, No. 2, 10 pages.
Michail, K., et al., "Development and validation of a liquid chromatographic method for the determination of hydroxymethylfurfural and alpha-ketoglutaric acid in human plasma", Analytica Chimica Acta, vol. 9, Issue 2, Jan. 2007, 11 pages.
Iwasaki, Yusuke, et al., "A new strategy for ionization enhancement by derivatization for mass spectrometry", Journal of Chromatography B, Elsevier, May 2011, 879, 7 pages.
EPO; Extended European Search Report for European Patent Application No. 18788060.4, dated Dec. 16, 2020, 11 pages.
EPO; Communication Pursuant to Rules 70(2) and 70a(2) EPC for European Patent Application No. 18788060.4, dated Jan. 19, 2021, 1 page.

\* cited by examiner

MASS SPECTROMETRY ASSAY METHOD FOR DETECTION AND QUANTITATION OF ORGANIC ACID METABOLITES

CROSS-REFERENCE TO RELATED APPLICATIONS

This application is a U.S. National Stage Application of International Patent Application No. PCT/US18/27734, filed on Apr. 16, 2018, which claims the benefit of U.S. Provisional Patent Application No. 62/487,542, filed on Apr. 20, 2017, the entire contents of which are hereby incorporated herein by reference.

BACKGROUND

The following information to describe the background of the invention is provided to assist the understanding of the invention and is not admitted to constitute or describe prior art to the invention.

Short chain fatty acids (SCFAs), as well as Lactate, are produced by bacteria in the colon during the fermentation of dietary fiber. After production, SCFAs are transported into the blood where they are taken up by organs and serve as substrates and signaling molecules to regulate energy homeostasis. SCFAs and their effects on energy metabolism have been linked to multiple disorders including inflammatory bowel disease, irritable bowel syndrome, diarrhea, metabolic syndrome, and cancer (Han, J. et al Analytica Chimica Acta. 854 (2015) 86-94 and Rio-Covián, D. et al. Front Microbiol. (2016) 7:185). Understanding the interplay between SCFAs and energy metabolism may help to better understand the microbiome, metabolism, and effects on disease.

Due to their volatility, SCFAs are not easily detected by LC-MS in their native state. SCFAs and other organic acids, including non-volatile organic acids such as Lactate, Pyruvate, and the intermediates of the tricarboxylic acid (TCA) cycle, are often poorly retained by traditional reverse phase liquid chromatography approaches and have reduced sensitivity with mass spectrometry detection. Consequently, these analytes are commonly detected by a combination of other methods, such as GC-MS and NMR. In the case of GC-based analysis, two separate methods are typically used: one method for the analysis of the volatile SCFAs and another method for non-volatile organic acids, which need to be derivatized prior to analysis.

There is a need for a reliable and reproducible method to measure volatile SCFAs together with non-volatile organic acids (such as lactate, pyruvate, TCA cycle intermediates) in a single analysis method. The methods described herein measure SCFAs and key energy metabolites (lactate, pyruvate, and the TCA cycle intermediates) of a sample in a single injection.

SUMMARY

In a first aspect of the invention, a method for determining in a sample, by mass spectrometry, the presence, absence, or amount of one or more analytes comprises multiple steps. The one or more analytes are selected from the group consisting of Acetic acid (C2), Propionic acid (C3), Butyric acid (C4), Isobutyric acid (C4), 2-Methyl-butyric acid (C5), Isovaleric acid (C5), Valeric acid (C5), Caproic acid (Hexanoic acid, C6), 3-Methylvaleric acid, 4-Methylvaleric acid (Isocaproic acid), Lactic acid, Pyruvic acid, Fumaric acid, Succinic acid, Malic acid, alpha-Ketoglutaric acid, Aconitic acid, Citric acid, Isocitric acid, and combinations thereof. The run time is less than six minutes. The method comprises subjecting the sample to an ionization source under conditions suitable to produce one or more ions detectable by mass spectrometry from each of the one or more analytes, wherein the one or more analytes are derivatized prior to ionization; measuring, in a single injection, by mass spectrometry, the amount of the one or more ions from each of the one or more analytes; and using the measured amount of the one or more ions to determine the amount of each of the one or more analytes in the sample.

In a second aspect of the invention, a method for determining in a sample, by mass spectrometry, the presence, absence, or amount of one or more analytes comprises multiple steps. The one or more analytes are selected from the group consisting of Acetic acid (C2), Propionic acid (C3), Butyric acid (C4), Isobutyric acid (C4), 2-Methyl-butyric acid (C5), Isovaleric acid (C5), Valeric acid (C5), Caproic acid (Hexanoic acid, C6), 3-Methylvaleric acid, 4-Methylvaleric acid (Isocaproic acid), and combinations thereof. The run time is less than six minutes. The method comprises subjecting the sample to an ionization source under conditions suitable to produce one or more ions detectable by mass spectrometry from each of the one or more analytes, wherein the one or more analytes are derivatized prior to ionization; measuring, in a single injection, by mass spectrometry, the amount of the one or more ions from each of the one or more analytes; and using the measured amount of the one or more ions to determine the amount of each of the one or more analytes in the sample.

In a third aspect of the invention, a method for determining in a sample, by mass spectrometry, the presence, absence, or amount of one or more analytes, wherein pivalic acid interference is eliminated, comprises multiple steps. The one or more analytes are selected from the group consisting of Acetic acid (C2), Propionic acid (C3), Butyric acid (C4), Isobutyric acid (C4), 2-Methyl-butyric acid (C5), Isovaleric acid (C5), Valeric acid (C5), Caproic acid (Hexanoic acid, C6), 3-methylvaleric acid, 4-methylvaleric acid (isocaproic acid), and combinations thereof. The method comprises subjecting the sample to an ionization source under conditions suitable to produce one or more ions detectable by mass spectrometry from each of the one or more analytes, wherein the one or more analytes are derivatized prior to ionization; measuring, in a single injection, by mass spectrometry, the amount of the one or more ions from each of the one or more analytes; and using the measured amount of the one or more ions to determine the amount of each of the one or more analytes in the sample.

In a fourth aspect of the invention, a method for determining in a sample, by mass spectrometry, the presence, absence, or amount of one or more analytes comprises multiple steps. The one or more analytes are selected from the group consisting of Lactic acid, Pyruvic acid, Fumaric acid, Succinic acid, Malic acid, alpha-Ketoglutaric acid, Aconitic acid, Citric acid, Isocitric acid, and combinations thereof. The run time is less than six minutes. The method comprises subjecting the sample to an ionization source under conditions suitable to produce one or more ions detectable by mass spectrometry from each of the one or more analytes, wherein the one or more analytes are derivatized prior to ionization; measuring, in a single injection, by mass spectrometry, the amount of the one or more ions from each of the one or more analytes; and using the measured amount of the one or more ions to determine the amount of each of the one or more analytes in the sample.

In features of these aspects, the amount of two or more analytes, three or more analytes, four or more analytes, or five or more analytes is determined. With regard to these features, one of the two or more analytes may be selected from the group consisting of: Acetic acid (C2), Propionic acid (C3), Butyric acid (C4), Isobutyric acid (C4), 2-Methyl-butyric acid (C5), Isovaleric acid (C5), Valeric acid (C5), Caproic acid (Hexanoic acid, C6), 3-Methylvaleric acid, 4-Methylvaleric acid (Isocaproic acid); and one of the two or more analytes may be selected from the group consisting of Lactic acid, Pyruvic acid, Fumaric acid, Succinic acid, Malic acid, alpha-Ketoglutaric acid, Aconitic acid, Citric acid, Isocitric acid, and combinations thereof. With additional regard to these features, one of the two or more analytes is Pyruvic acid.

In a further feature of the aspects, the sample is derivatized using at least 2,4-Difluorophenyl Hydrazine Hydrochloride or 3-Nitrophenylhydrazine Hydrochloride. In an additional feature of the aspects, the sample is derivatized using at least 2,4-Difluorophenyl Hydrazine Hydrochloride and wherein the sample is a fecal sample. In another feature of the aspects, the sample is derivatized using at least 3-Nitrophenylhydrazine Hydrochloride and wherein the sample is a plasma sample. With regard to this feature, one or more coupling catalysts selected from the group consisting of EDC Hydrocholoride, 1-Hydroxybenzotriazole, N,N' diisopropylcarbodiimide (DIC), and dicyclohexylcarbodiimide (DCC), is also used for derivatization.

With further regard to the above features, the amount of Acetic acid (C2), Propionic acid (C3), and Butyric acid (C4) may be determined, the amount Acetic acid (C2), Propionic acid (C3), Butyric acid (C4) and lactic acid may be determined, the amount Acetic acid (C2), Propionic acid (C3), Isobutyric acid (C4), and Butyric acid (C4) may be determined, and the amount Acetic acid (C2), Propionic acid (C3), Isobutyric acid (C4), Butyric acid (C4), 2-Methyl-butyric acid (C5), Isovaleric acid (C5), Valeric acid (C5), and Caproic acid (Hexanoic acid, C6), may be determined.

In a feature of the above aspects, the mass spectrometer is operated in negative mode. In an additional feature, the sample has been purified by liquid chromatography prior to being subjected to an ionization source. With regard to this feature, the liquid chromatography is selected from the group consisting of high performance liquid chromatography, ultra high performance liquid chromatography, and turbulent flow liquid chromatography. With further regard to this feature, the sample has been purified by either high performance liquid chromatography or ultrahigh performance liquid chromatography prior to being subjected to an ionization source.

In a further feature of the aspects, an internal standard is used to determine the amount of the one or more analytes in the sample. With regard to this feature, the internal standard comprises an isotopically labeled analog of at least one of the one or more analytes to be measured. In an additional feature, the sample comprises a biological sample. With regard to this feature, the sample is selected from the group consisting of blood, plasma, urine, feces, bacterial culture supernatant, serum, breast milk, saliva, and tissue.

In another feature of the aspects, the one or more ions used to determine the amount of each of the one or more analytes are one or more ions selected from the ions in Tables 4 and 5. In yet a further feature, the mass spectrometry is tandem mass spectrometry.

In a fifth aspect of the invention, a kit comprises one or more isotopically labeled analogues as internal standards for each of one or more analytes. The one or more analytes are selected from the group consisting of Acetic acid (C2), Propionic acid (C3), Isobutyric acid (C4), Butyric acid (C4), 2-Methyl-butyric acid (C5), Isovaleric acid (C5), Valeric acid (C5), Caproic acid (Hexanoic acid, C6), Lactic acid, Pyruvic acid, Fumaric acid, Succinic acid, Malic acid, alpha-Ketoglutaric acid, Aconitic acid, Citric acid, Isocitric acid, and combinations thereof. The kit also comprises packaging material and instructions for using the kit.

In a feature of this aspect, the kit further comprises derivatization reagents, catalyst reagents, calibration standards, or quality control samples.

DETAILED DESCRIPTION

Figure 1:
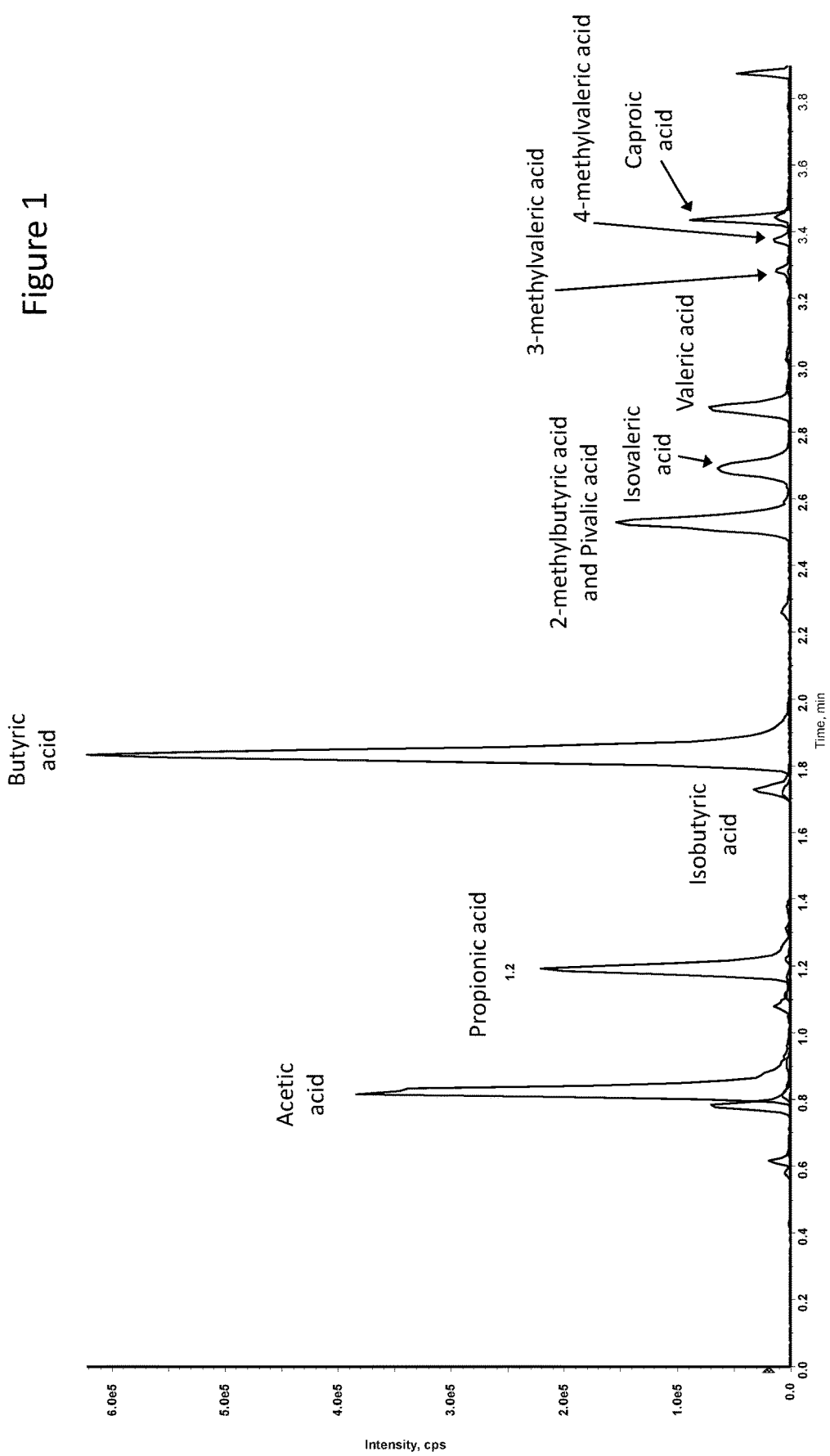
FIG. 1 shows an example chromatogram of Acetic acid (C2), Propionic acid (C3), Isobutyric acid (C4), Butyric acid (C4), 2-Methyl-butyric acid (C5), Isovaleric acid (C5), Valeric acid (C5), 3-Methylvaleric acid, 4-Methylvaleric acid, and Caproic acid (Hexanoic acid, C6), in a single chromatogram generated from the analysis of calibration standard samples using Derivatization Procedure 3 and the LC-MS methods described herein. Pivalic acid is not separated from 2-Methyl-butyric acid.

Methods are described for detecting the presence, absence, or amount of one or more analytes selected from the group consisting of: Acetic acid (C2), Propionic acid (C3), Isobutyric acid (C4), Butyric acid (C4), 2-Methyl-butyric acid (C5), Isovaleric acid (C5), Valeric acid (C5), Caproic acid (Hexanoic acid, C6), Pivalic acid, 3-Methylvaleric acid, 4-Methylvaleric acid (Isocaproic acid), Lactic acid, Pyruvic acid, Fumaric acid, Succinic acid, Malic acid, alpha-Ketoglutaric acid, Aconitic acid, Citric acid, Isocitric acid, and combinations thereof, in a sample. The "energy metabolites" detected using the methods described herein include Lactic acid, Pyruvic acid, Fumaric acid, Succinic acid, Malic acid, alpha-Ketoglutaric acid, Aconitic acid, Citric acid, Isocitric acid. The "TCA cycle intermediates" detected using the methods described herein include Fumaric acid, Succinic acid, Malic acid, alpha-Ketoglutaric acid, Aconitic acid, Citric acid, Isocitric acid.

Suitable samples for use in the methods described herein include any material or complex mixture of interest. In one embodiment, the sample may be a biological sample, for example a biological fluid, biological solid or tissue. Non-limiting examples of biological samples include blood (whole blood), blood plasma (plasma), blood serum (serum), urine, cerebral spinal fluid (CSF), breast milk, saliva, feces, cells (animal or plant), cell cultures (animal or plant), animal or plant cell culture supernatant, bacterial culture supernatant, bacterial cells, or plant or animal tissue (include gut tissue and gut contents). The biological sample may be obtained from any biological source such as an animal, a plant, a cell culture, etc. The animal may be a mammalian animal such as, for example, a human, monkey, mouse, rabbit or rat or a non-mammalian animal such as, for example, a fish. The plant may be any plant, including agriculturally useful plants.

Mass spectrometric methods are described for detecting the presence, absence, or amount of one or more analytes in a sample using a single injection. The methods may use a liquid chromatography step such as UPLC to perform a separation (purification, enrichment) of selected analytes combined with mass spectrometry, thereby providing a high-throughput assay system for quantifying a plurality of analytes in a sample that is amenable to automation.

One obstacle to the accurate quantitation of analytes when using LC/MS is interference from co-eluting analytes. One such interfering analyte is Pivalic acid which co-elutes with C5 SCFAs (2-Methyl-butyric acid, Isovaleric acid, Valeric acid) and can lead to the inaccurate quantitation of those analytes. Pivalic acid is a xenobiotic that is found in plastics and may be present in biological samples as an environmental background contaminant. It can also be formed in-vivo from the metabolism of drugs containing pivaloyl ester residues, such as certain antibiotics. The methods described herein overcome this interference and separate the SCFA analytes from Pivalic acid either chromatographically, by selection of the appropriate Derivatization Procedure, for example, Derivatization Procedure 2, or by using daughter ions that are not formed by Pivalic acid for detection of these analytes.

The described methods: 1) quantitatively measure the amount of SCFA analytes, Lactate, Pyruvate, and TCA cycle intermediates in a single injection; 2) improve sensitivity compared to standard methods 3) overcome interference due to Pivalic acid; 4) improve the accuracy of quantitation of C5-SCFA metabolites; 5) have a run time, including chromatography and mass spectrometry, of less than 6 minutes which may serve to increase instrument capacity; and 6) use a single injection for the analysis which may conserve resources and increase throughput.

An advantage of the described methods is the ability to separate and measure the presence, absence, or amount of one or more SCFA analytes selected from the group consisting of Acetic acid (C2), Propionic acid (C3), Isobutyric acid (C4), Butyric acid (C4), 2-Methyl-butyric acid (C5), Isovaleric acid (C5), Valeric acid (C5), Caproic acid (Hexanoic acid, C6), 3-Methylvaleric acid, 4-Methylvaleric acid (Isocaproic acid); and one or more energy metabolites selected from the group consisting of Lactic acid, Pyruvic acid, Fumaric acid, Succinic acid, Malic acid, alpha-Ketoglutaric acid, Aconitic acid, Citric acid, Isocitric acid in a single injection using liquid chromatography-mass spectrometry.

Another advantage of these methods is the ability to measure SCFAs and energy metabolites in a single injection while separating all 20 metabolites including the ability to separate Pivalic acid from 2-Methylbutyric acid within a shorter run time than published methods (Han et al.). In instances where Pivalic acid is not separated from 2-Methylbutyric acid chromatographically, interference from Pivalic acid can be overcome by using a daughter ion for detection of 2-Methylbutyric acid that is not formed by Pivalic acid. Combinations of one or more and up to 20 metabolites selected from the group consisting of Acetic acid (C2), Propionic acid (C3), Isobutyric acid (C4), Butyric acid (C4), 2-Methyl-butyric acid (C5), Isovaleric acid (C5), Valeric acid (C5), Caproic acid (Hexanoic acid, C6), 3-Methylvaleric acid, 4-Methylvaleric acid (Isocaproic acid), Pivalic acid, Lactic acid, Pyruvic acid, Fumaric acid, Succinic acid, Malic acid, alpha-Ketoglutaric acid, Aconitic acid, Citric acid, and Isocitric acid can be detected in a single injection with a run time of less than 6 minutes.

The methods presented herein provide additional advantages over current methods used to measure SCFAs and energy metabolites (including Lactate, Pyruvate, and the TCA cycle intermediates). The ability to measure, in a single injection, a plurality of analytes in various combinations, reduces the time required to obtain analysis results, uses fewer resources in terms of laboratory disposables (e.g., tubes, pipette tips, reagents), laboratory instruments and human resources. These improvements lead to savings by decreasing the costs of the assays and increasing the instrument and laboratory capacity for sample analysis.

Prior to describing this invention in further detail, the following terms are defined.

Definitions

The term "separation" refers to the process of separating a complex mixture into its component molecules or metabolites. Common, exemplary laboratory separation techniques include electrophoresis and chromatography.

The term "chromatography" refers to a physical method of separation in which the components (i.e., chemical constituents) to be separated are distributed between two phases, one of which is stationary (stationary phase) while the other (the mobile phase) moves in a definite direction. The mobile phase may be gas ("gas chromatography", "GC") or liquid ("liquid chromatography", "LC"). Chromatographic output data may be used in embodiments of the method described herein.

The term "liquid chromatography" or "LC" refers to a process of selective inhibition of one or more components of a fluid solution as the fluid uniformly moves through a column of a finely divided substance or through capillary passageways. The inhibition results from the distribution of the components of the mixture between one or more stationary phases and the mobile phase(s) as the mobile phase(s) move relative to the stationary phase(s). Examples of "liquid chromatography" include "Reverse phase liquid chromatography" or "RPLC", "high performance liquid chromatography" or "HPLC", "ultra-high performance liquid chromatography" or "UPLC" or "UHPLC".

The term "retention time" refers to the elapsed time in a chromatography process since the introduction of the sample into the separation device. The retention time of a constituent of a sample refers to the elapsed time in a chromatography process between the time of injection of the sample into the separation device and the time that the constituent of the sample elutes (e.g., exits from) the portion of the separation device that contains the stationary phase.

The term "retention index" of a sample component refers to a number, obtained by interpolation (usually logarithmic), relating the retention time or the retention factor of the sample component to the retention times of standards eluted before and after the peak of the sample component, a mechanism that uses the separation characteristics of known standards to remove systematic error.

The term "Mass Spectrometry" (MS) refers to a technique for measuring and analyzing molecules that involves ionizing or ionizing and fragmenting a target molecule, then analyzing the ions, based on their mass/charge ratios, to produce a mass spectrum that serves as a "molecular fingerprint". Determining the mass/charge ratio of an object may be done through means of determining the wavelengths at which electromagnetic energy is absorbed by that object. There are several commonly used methods to determine the mass to charge ratio of an ion, some measuring the interaction of the ion trajectory with electromagnetic waves, others measuring the time an ion takes to travel a given distance, or a combination of both. The data from these fragment mass measurements can be searched against databases to obtain identifications of target molecules.

The terms "operating in negative mode" or "operating in negative multiple reaction monitoring (MRM) mode" or "operating in negative ionization mode" refer to those mass spectrometry methods where negative ions are generated and detected. The terms "operating in positive mode" or "operating in positive MRM mode" or "operating in positive ionization mode" refer to those mass spectrometry methods where positive ions are generated and detected.

The term "mass analyzer" refers to a device in a mass spectrometer that separates a mixture of ions by their mass-to-charge ("m/z") ratios.

The term "m/z" refers to the dimensionless quantity formed by dividing the mass number of an ion by its charge number. It has long been called the "mass-to-charge" ratio.

As used herein, the term "source" or "ionization souce" refers to a device in a mass spectrometer that ionizes a sample to be analyzed. Examples of ionization sources include electrospray ionization (ESI), atmospheric pressure chemical ionization (APCI), heated electrospray ionization (HESI), atmospheric pressure photoionization (APPI), flame ionization detector (FID), matrix-assisted laser desorption ionization (MALDI), etc.

As used herein, the term "detector" refers to a device in a mass spectrometer that detects ions.

The term "ion" refers to any object containing a charge, which can be formed for example by adding electrons to or removing electrons from the object.

The term "mass spectrum" refers to a plot of data produced by a mass spectrometer, typically containing m/z values on x-axis and intensity values on y-axis.

The term "scan" refers to a mass spectrum that is associated with a particular separation index. For example, systems that use a chromatographic separation technique may generate multiple scans, each scan at a different retention time.

The term "run time", refers to the time from sample injection to generation of the instrument data. The total run time for a sample includes chromatography analysis and mass spectrometry analysis.

The term "tandem MS" refers to an operation involving multiple stages of MS selection with fragmentation occurring between the stages. In a first MS stage, ions are formed in the source and are separated by mass-to-charge ratio. Ions, of a particular mass-to-charge ratio, each representing one (and possibly more than one) chemical constituent, are selected, and fragment ions are created. The resulting fragment ions are then separated and detected in a second stage of mass spectrometry. The ion of interest in the first MS stage corresponds to a "parent" or precursor ion, while the ions created during the second MS stage(s) correspond to sub-components of the parent ion and are herein referred to as "daughter" or "product" ions.

Thus, tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion. Tandem MS may be repeated on daughter ions to determine "grand-daughter" ions, for example. Thus, tandem MS is not limited to two-levels of fragmentation, but is used generically to refer to multi-level MS, also referred to as "MS$^n$". The term "MS/MS" is a synonym for "MS$^2$". For simplicity, the term "daughter ion" hereinafter refers to any ion created by a secondary or higher-order (i.e., not the primary) MS.

The term "derivatize" means to react two molecules to form a new molecule. A derivatized analyte is an analyte that has been reacted with a reagent (e.g., a derivatization reagent) for the purpose of, for example, facilitating purification, ionization, fragmentation, detection, or any combination thereof. In some examples, a "coupling catalyst" may be used with the derivatization reagent to facilitate derivatization of the analyte.

The "amount" of one or more analytes means the absolute amount or concentration of the analyte measured in the sample. For example, the amount or concentration may be expressed as the molar concentration, mass fraction, mole fraction, molality, or percentage.

I. Sample Preparation and Quality Control (QC)

Sample extracts containing analytes are prepared by isolating the analytes in the sample from the macromolecules (e.g., proteins, nucleic acids, lipids) that may be present in the sample. The terms "sample extracts", "extracted samples" or "analyte extracts" may also be referred to herein as "analytical samples" and the terms may be used interchangeably. Some or all analytes in a sample may be bound to proteins. Various methods may be used to disrupt the interaction between analyte(s) and protein prior to MS analysis. For example, the analytes may be extracted from a sample to produce a liquid extract, while the proteins that may be present are precipitated and removed. Proteins may be precipitated using, for example, a solution of methanol, acetonitrile, or ethyl acetate. To precipitate the proteins in the sample, a methanol, acetonitrile, or ethyl acetate solution is added to the sample, then the mixture may be spun in a centrifuge to separate the liquid supernatant (containing the extracted analytes) from the precipitated proteins.

In other embodiments, analytical samples are prepared by releasing the analytes from protein without precipitating the protein. For example, a formic acid solution may be added to the sample to disrupt the interaction between protein and analyte. Alternatively, ammonium sulfate, a solution of formic acid in ethanol, or a solution of formic acid in methanol may be added to the sample to disrupt ionic interactions between protein and analyte without precipitating the protein.

Analytical samples may be derivatized using an appropriate derivatization reagent and coupling catalyst. In one example, samples may be derivatized using 2,4-Difluorophenyl Hydrazine Hydrochloride and a coupling catalyst. In another example, samples may be derivatized using 3-Nitrophenylhydrazine Hydrochloride and a coupling catalyst. The coupling catalyst may be, for example, 1-(3-dimethylaminopropyl)-3-ethylcarbodiimide hydrochloride (EDC hydrochloride), N,N' diisopropylcarbodiimide (DIC), dicyclohexylcarbodiimide (DCC), DIC in combination with 1-hydroxybenzotriazole (HOBt), or DCC in combination with 1-hydroxybenzotriazole (HOBt). In some examples, a base such as pyridine or triethylamine or similar bases may be added to the derivatization mixture. In one example, the derivatization reagent may be 2,4-Difluorophenyl Hydrazine Hydrochloride and the coupling catalyst may be DIC in combination with HOBt and pyridine. In another example, the derivatization reagent may be 2,4-Difluorophenyl Hydrazine Hydrochloride and the coupling catalyst may be EDC hydrochloride. In yet another example, the derivatization reagent may be 3-Nitrophenylhydrazine Hydrochloride and the coupling catalyst may be DIC in combination with HOBt and pyridine. The concentration of 2,4-Difluorophenyl Hydrazine Hydrochloride and 3-Nitrophenylhydrazine Hydrochloride may range from 1 to 200 mg/mL. The concentration of EDC Hydrochloride and DCC may range from 1 to 100 mg/mL. The concentration of DIC may range from 1-100%. In some examples, 0.5-5 µl of 100% DIC (or a solution of the corresponding amount) may be added directly to the samples. The concentration of pyridine, may range from 1-100%. In some examples, 0.5-5 µl of 100% pyridine (or a solution of the corresponding amount) may be added directly to the samples. In one example, the concentration of 2,4-Difluorophenyl Hydrazine Hydrochloride may be 25 mg/mL, the concentration of HOBt may be 25 mg/mL, and 2 µl of 100% DIC and 2 µL of 100% pyridine may be added to the samples. In another example, the concentration of 2,4-Difluorophenyl Hydrazine Hydrochloride and the concentration of EDC hydrochloride may be 25 mg/mL. In yet another example, the concentration of 3-Nitrophenylhydrazine Hydrochloride may be 25 mg/mL, the concentration of HOBt may be 25 mg/mL, and 2 µl of 100% DIC and 2 µL of 100% pyridine may be added to the samples. The derivatization reagent used in the methods described herein may be selected based on the sample type to be analyzed. In one example, the derivatization reagent 2,4-Difluorophenyl Hydrazine Hydrochloride may be selected for the analysis of fecal samples. In another example, the derivatization reagent 3-Nitrophenylhydrazine Hydrochloride may be selected for the analysis of plasma samples.

In some embodiments the analytical sample may be subjected to various methods including liquid chromatography, electrophoresis, filtration, centrifugation, and affinity separation as described herein to purify or enrich the amount of the selected analyte relative to one or more other components in the sample.

To assess precision, accuracy, calibration range, or analytical sensitivity of methods of detecting and quantifying analytes, quality control (QC) samples may be used. The concentration of a given analyte(s) to be used in a QC sample may be determined based on lower limit of quantitation (LLOQ) or upper limit of quantitation (ULOQ) of the given analyte(s), as detected in a sample. In one example, the LLOQ may be represented by the concentration of a standard (e.g., Standard A), and the ULOQ may be represented by the concentration of a second standard (e.g., Standard H). The Low QC value may be set at a concentration of about 3 X LLOQ, the Mid QC value may be at a concentration of about 25-50% of High QC, and the High QC value may be at a concentration of about 80% of the ULOQ. The QC target concentration levels may be chosen based on a combination of the Analytical Measurement Range (AMR) and the frequency of sample results as measured in a set of representative samples.

II. Chromatography

Prior to mass spectrometry, the analytical sample may be subjected to one or more separation methods such as electrophoresis, filtration, centrifugation, affinity separation, or chromatography. In one embodiment the separation method may comprise liquid chromatography (LC), including, for example, ultra high performance LC (UHPLC).

In some embodiments, UHPLC may be conducted using a reversed phase column chromatographic system, hydrophilic interaction chromatography (HILIC), or a mixed phase column chromatographic system.

The column heater (or column manager) for LC may be set at a temperature of from about 25° C. to about 80° C. For example, the column heater may be set at about 40° C., 50° C., 60° C., 70° C., etc.

In an example, UHPLC may be conducted using HILIC system. In another example, UHPLC may be conducted using a reversed phase column chromatographic system. The system may comprise two or more mobile phases. Mobile phases may be referred to as, for example, mobile phase A, mobile phase B, mobile phase A', and mobile phase B'.

In an exemplary embodiment using two mobile phases, A and B, mobile phase A may comprise formic acid and water, and mobile phase B may comprise formic acid and acetonitrile. The concentration of formic acid in mobile phase A or mobile phase B may range from 0.001% to 5%. The concentration of acetonitrile may range from 0% to 100%. For example, mobile phase A may comprise 0.005, 0.01, 0.05, 0.1, or 0.5% formic acid in water and mobile phase B may comprise 0.005, 0.01, 0.05, 0.1, or 0.5% formic acid in acetonitrile.

In one example, linear gradient elution may be used for chromatography. The starting conditions for linear gradient elution may include the concentration of a mobile phase (e.g., mobile phase A) and/or the flow rate of a mobile phase through the column (e.g., mobile phase A). The starting conditions may be optimized for the separation and/or retention of one or more analytes. The gradient conditions may also be optimized for the separation and/or retention of analytes and may vary depending on the flow rate selected. For example, initial conditions may be 20% mobile phase B and 800 µL/min flow rate. Mobile phase B may be maintained at 20% for 3-4 min, increased to 30-60%, maintained for 0.5-1 min, then increased to 70-90%, and maintained at 70-90% for less than a minute. Mobile phase B may revert to 20% at 5.0 min where it may be maintained for less than a minute for equilibration for the next sample injection. The total run time may be less than six minutes.

Chromatography conditions may be optimized to allow a faster flow rate without losing resolution, which allows a shorter run time and thereby increases instrument capacity. For example, gradient conditions may be optimized to allow a faster flow rate and retain resolution. In another example, the temperature of the column heater may be optimized to allow a faster flow rate without decreasing the resolution. In another example the temperature and gradient conditions may be optimized to allow a faster flow rate while retaining resolution. In an example, chromatography conditions can be optimized for a total run time of less than six minutes by setting the column heater at 60 ° C. and using a gradient profile with initial conditions of 20% mobile phase B and 800 µL/min flow rate.

The eluent from the chromatography column may be directly and automatically introduced into the electrospray source of a mass spectrometer. The total run time, including chromatography and mass spectrometry, to determine the presence, absence, or amount of one or more analytes selected from the group consisting of Acetic acid (C2), Propionic acid (C3), Isobutyric acid (C4), Butyric acid (C4), 2-Methyl-butyric acid (C5), Isovaleric acid (C5), Valeric acid (C5), 3-Methylvaleric acid, 4-Methylvaleric acid (Isocaproic acid), Caproic acid (Hexanoic acid, C6), Pivalic acid, Lactic acid, Pyruvic acid, Fumaric acid, Succinic acid, Malic acid, alpha-Ketoglutaric acid, Aconitic acid, Citric acid, and Isocitric acid may be less than six minutes.

III. Mass Spectrometry and Quantitation

One or more analytes may be ionized by, for example, mass spectrometry. Mass spectrometry is performed using a mass spectrometer that includes an ion source for ionizing the fractionated sample and creating charged molecules for further analysis. Ionization may be performed by, for example, electrospray ionization (ESI). Other ion sources may include, for example, atmospheric pressure chemical ionization (APCI), heated electrospray ionization (HESI), atmospheric pressure photoionization (APPI), flame ionization detector (FID), or matrix-assisted laser desorption ionization (MALDI). The choice of ionization method may be determined based on a number of considerations. Exemplary considerations include the analyte to be measured, type of sample, type of detector, and the choice of positive or negative mode.

The one or more analytes may be ionized to create one or more ions. For example, the analytes Acetic acid (C2), Propionic acid (C3), Isobutyric acid (C4), Butyric acid (C4), 2-Methyl-butyric acid (C5), Isovaleric acid (C5), Valeric acid (C5), 3-Methylvaleric acid, 4-Methylvaleric acid (Isocaproic acid), Caproic acid (Hexanoic acid, C6), Pivalic acid, Lactic acid, Pyruvic acid, Fumaric acid, Succinic acid, Malic acid, alpha-Ketoglutaric acid, Aconitic acid, Citric acid, and Isocitric acid may be ionized in negative mode.

Mass spectrometer instrument settings may be optimized for the given method and/or for the particular mass spectrometer used. The instrument may use various gases, for example, nitrogen, helium, argon, or zero air. Mass spectrometry may be performed using AB Sciex QTrap 5500 mass spectrometers. In one example, the mass spectrometer may be operated in negative multiple reaction monitoring (MRM) mode. The ionspray voltage setting may range from about −0.5 kV to about −5.0 kV; in one embodiment the voltage may be set at −4.5 kV. The source temperature may range from about 250° C. to about 750° C.; in one embodiment the source temperature may be set at 500° C. The curtain gas may range from about 10 to about 55 psi; in one embodiment the curtain gas is set at 30 psi. The nebulizer and desolvation gas flow rates may range from about 0 to about 90 psi. In one embodiment the flow rates may be set at 70. The collisionally activated dissociation (CAD) gas setting may range from high to low; in one embodiment the CAD gas is set at medium. Declustering potential may range from about −75V to about −40V. The collision energy (CE) may range from about −70 eV to about −10 eV. The entrance potential (EP) setting may range from about −20V to about −5V. The collision cell exit potential (CXP) setting may range from about −20V to about −5V.

Following ionization, the charged ions may be analyzed to determine a mass-to-charge ratio. Exemplary suitable analyzers for determining mass-to-charge ratios include quadrupole analyzers, ion trap analyzers, and time of flight analyzers. The ions may be detected using, for example, a selective mode or a scanning mode. Exemplary scanning modes include MRM and selected reaction monitoring (SRM).

Analysis results may include data produced by tandem MS. In exemplary embodiments, tandem MS may be accurate-mass tandem MS. For example, the accurate-mass tandem mass spectrometry may use a quadrupole time-of-flight (Q-TOF) analyzer. Tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion.

For example, a primary mass spectrum may contain five distinct ions, which may be represented as five graphical peaks. Each ion in the primary MS may be a parent ion. Each parent ion may be subjected to a secondary MS that produces a mass spectrum showing the daughter ions for that particular parent ion.

The parent/daughter relationship may be extended to describe the relationship between separated components (e.g., components eluting from the chromatography state) and ions detected in the primary MS, and to the relationship between the sample to be analyzed and the separated components.

The mass spectrometer typically provides the user with an ion scan (i.e., a relative abundance of each ion with a particular mass/charge over a given range). Mass spectrometry data may be related to the amount of the analyte in the original sample by a number of methods. In one example, a calibration standard is used to generate a standard curve (calibration curve) so that the relative abundance of a given ion may be converted into an absolute amount of the analyte represented by that ion. In another example, the calibration standard may be an external standard and a standard curve may be generated based on ions generated from those standards to calculate the quantity of one more analytes. In a further example, the external standard may be an unlabeled analyte.

Internal standards may be added to calibration standards and/or test samples. An internal standard may be used to account for loss of analytes during sample processing in order to get a more accurate value of a measured analyte in the sample. The ratio of analyte peak area to internal standard peak area in the levels of the calibration standards may be used to generate a calibration curve and quantitate samples. One or more isotopically labeled analogs of analytes, for example, Acetic acid-$d_3$, Propionic acid-$d_5$, Isobutyric acid-$d_3$, Butyric acid-$d_3$, 2-Methyl-butyric acid-$d_3$, Isovaleric acid-$d_9$, Valeric acid-$d_3$, Hexanoic acid-$d_3$, Trimethyl-$d_9$-acetic acid (Pivalic acid $d_9$), 3-Methylpentanoic-$d_{11}$ acid, 4-Methylpentanoic-$d_{11}$ acid, Lactic acid-$d_4$, Pyruvic acid-$^{13}C_3$, α-Ketoglutaric acid-$^{13}C_4$, Citric acid-$d_4$, Malic acid-$d_3$, Fumaric acid-$^{13}C_4$, and Succinic acid-$d_4$ may be used as internal standards. In some examples, an isotopically labeled analog may not be available for all analytes, and an isotopically labeled analog for an analyte of similar structure may be used. For example, for quantitation of Aconitic acid and Isocitric acid, Citric acid-$d_4$ may be used. The one or more internal standards may be combined in a solution, for example, a working internal standard (WIS) solution. The WIS solution may be comprised of one or more internal standards and may comprise one or more internal standards for each of the analytes to be measured.

The analysis data from the MS instrument may be sent to a computer and processed using computer software. In one example, peak area ratios of analyte to internal standard are fitted against the concentrations of the calibration standards using a statistical regression method for quantitation. In another example, the statistical regression is weighted linear least squares regression. The slope and intercept calculated using the calibration curve may be used to calculate the unknown concentrations of analytes in experimental samples.

IV. Kit

A kit for assaying one or more analytes selected from the group consisting of Acetic acid (C2), Propionic acid (C3), Isobutyric acid (C4), Butyric acid (C4), 2-Methyl-butyric acid (C5), Isovaleric acid (C5), Valeric acid (C5), and Caproic acid (Hexanoic acid, C6), 3-Methylvaleric acid, 4-Methylvaleric acid (Isocaproic acid), Pivalic acid, Lactic acid, Pyruvic acid, Fumaric acid, Succinic acid, Malic acid, alpha-Ketoglutaric acid, Aconitic acid, Citric acid, and Isocitric acid and combinations thereof is described herein. For example, a kit may include packaging material, a derivatization reagent, catalyst reagents and measured amounts of one or more calibration standards or internal standards or quality control samples in amounts sufficient for one or more assays. In exemplary embodiments, the internal standards may be isotopically labeled, the kit may comprise pre-made, calibration standard solutions, internal standard solutions, catalyst reagent solutions, mobile phase solutions, quality control samples, quality control sample reconstitution solutions and/or the kit may comprise calibration standard reagents, internal standard reagents, catalyst reagents, mobile phase reagents, and instructions to prepare calibration standard solutions, internal standard solutions, catalyst reagent solutions, mobile phase solutions and quality control samples. Kits may also comprise instructions recorded in tangible form (e.g. on paper such as, for example, an instruction booklet or an electronic medium) for using the reagents to measure the one or more analytes.

EXAMPLES

I. Reagents and Instruments

Sodium acetate, Sodium propionate, Isobutyric acid, Sodium butyrate, 2-Methyl-butyric acid, Isovaleric acid, Valeric acid, Hexanoic acid, Sodium acetate-$d_3$, formic acid, N,N' Diisopropylcarbodiimide (DIC), Dicyclohexylcarbodiimide (DCC), 1-Hydroxybenzotriazole (HOBt) and Pyridine were obtained from Sigma-Aldrich; Sodium propionate-$d_5$, Isobutyric acid-$d_3$, Sodium butyrate-$d_3$, 2-Methyl-butyric acid-$d_3$, Isovaleric acid-$d_9$, Valeric acid-$d_3$, Hexanoic acid-$d_3$, Sodium lactate acid-$d_4$, Malic acid-$d_3$, and Succinic acid-$d_4$ were obtained from CDN Isotopes; Sodium pyruvate-$^{13}C_3$, Fumaric acid-$^{13}C_4$, Citric acid-$d_4$ and Disodium α-ketoglutarate-$^{13}C_4$, were obtained from Cambridge Isotope Laboratories; and 1-(3-Dimethylaminopropyl)-3-Ethylcarbodiimide hydrochloride (EDC hydrochloride) and 2,4-Difluorophenyl Hydrazine Hydrochloride were obtained from TCI America. HPLC grade methanol was obtained from Fisher Scientific; HPLC grade acetonitrile and HPLC grade water were obtained from Acros. A Multi-Tube Vortexer from VWR Scientific was used for mixing. Centrifugation of plates was carried out in a Sorvall ST 40R centrifuge from Thermo Scientific with a 3617 bucket rotor.

II. Internal Standard Preparation

Working internal standard (WIS) solutions were prepared at the concentrations indicated in Table 1 in water (for Sodium acetate-$d_3$, Sodium propionate-$d_5$, Isobutyric acid-$d_3$ and Sodium butyrate-$d_3$, Sodium lactate acid-$d_4$, Sodium pyruvate-$^{13}C_3$, Disodium α-ketoglutarate-$^{13}C_4$, Citric acid-$d_4$, Malic acid-$d_3$, Fumaric acid-$^{13}C_4$, Succinic acid-$d_4$) or in methanol:water (1:1) (for 2-Methyl-butyric acid-$d_3$, Isovaleric acid-$d_9$, Valeric acid-$d_3$, Hexanoic acid-$d_3$). Labeled internal standards were not available for Aconitic acid or Isocitric acid, and the structurally similar standard Citric acid-$d_4$ was used for quantitation of those analytes.

TABLE 1

| Working Internal Standard (WIS) Solutions | |
|---|---|
| Internal Standard Name | Concentration (μg/mL) |
| Acetic acid-$d_3$ | 625 |
| Propionic acid-$d_5$ | 5.00 |
| Isobutyric acid-$d_3$ | 5.00 |
| Butyric acid-$d_3$ | 50.0 |
| 2-Methyl-butyric acid-$d_3$ | 5.00 |
| Isovaleric acid-$d_9$ | 5.00 |
| Valeric acid-$d_3$ | 5.00 |
| Hexanoic acid-$d_3$ | 5.00 |
| Lactic acid-$d_4$ | 5.00 |
| Pyruvic acid-$^{13}C_3$ | 1.00 |
| Fumaric acid-$^{13}C_4$ | 1.00 |
| Succinic acid-$d_4$ | 1.00 |
| Malic acid-$d_3$ | 1.00 |
| α-Ketoglutaric acid-$^{13}C_4$ | 1.00 |
| Citric acid-$d_4$ | 1.00 |

III. Determination of Calibration Range

The calibration range of each analyte for an indicated sample type was determined using solutions spiked with known concentrations of calibration standards. Calibration spiking solutions were prepared at 20-fold of the corresponding calibration concentrations. For example, for representative analytes, the final analyte concentrations in each calibration standard are listed in Tables 2 and 3, for bacterial culture supernatant and fecal samples, respectively. One of ordinary skill in the art would understand how to determine the calibration range for additional analytes and in additional sample types without undue experimentation. For each analyte, the LLOQ represents the low end of the calibration range, and the high end of the calibration range is represented by the ULOQ. To cover the calibration ranges of the indicated sample types, ten calibration standards (standards A-J in Table 2) were used for analyzing bacterial culture supernatant samples, and eight calibration standards (standards A-H in Table 3) were used for analyzing fecal samples.

TABLE 2

Calibration Ranges for Analytes in Bacterial Culture Supernatant Samples

| Analyte | Concentration (μg/mL) | | | | | | | | | |
|---|---|---|---|---|---|---|---|---|---|---|
| | A | B | C | D | E | F | G | H | I | J |
| Acetic Acid | n/a | 62.5 | 125 | 250 | 500 | 1000 | 2500 | 3750 | 5000 | 6250 |
| Propionic Acid | n/a | n/a | 1 | 2 | 4 | 8 | 20 | 30 | 40 | 50 |
| Isobutyric Acid | n/a | n/a | 1 | 2 | 4 | 8 | 20 | 30 | 40 | 50 |
| Butyric Acid | n/a | n/a | 4 | 8 | 16 | 50 | 200 | 800 | 1600 | 2000 |
| 2-Methylbutyric Acid | n/a | n/a | 1 | 2 | 4 | 8 | 20 | 30 | 40 | 50 |
| Isovaleric Acid | n/a | n/a | 1 | 2 | 4 | 8 | 20 | 30 | 40 | 50 |
| Valeric Acid | 0.25 | 0.5 | 1 | 2 | 4 | 8 | 20 | 30 | 40 | 50 |
| Hexanoic Acid | n/a | 0.5 | 1 | 2 | 4 | 8 | 20 | 30 | 40 | 50 |

TABLE 3

Calibration Ranges for Analytes in Fecal Samples

| Analyte | Concentration (μg/mL) | | | | | | | |
|---|---|---|---|---|---|---|---|---|
| | A | B | C | D | E | F | G | H |
| Acetic Acid | 200 | 400 | 800 | 2000 | 5000 | 10000 | 16000 | 20000 |
| Propionic Acid | 100 | 200 | 400 | 1000 | 2500 | 5000 | 8000 | 10000 |
| Isobutyric Acid | 20 | 40 | 80 | 200 | 500 | 1000 | 1600 | 2000 |
| Butyric Acid | 100 | 200 | 400 | 1000 | 2500 | 5000 | 8000 | 10000 |
| 2-Methylbutyric Acid | 20 | 40 | 80 | 200 | 500 | 1000 | 1600 | 2000 |
| Isovaleric Acid | 20 | 40 | 80 | 200 | 500 | 1000 | 1600 | 2000 |
| Valeric Acid | 20 | 40 | 80 | 200 | 500 | 1000 | 1600 | 2000 |
| Hexanoic Acid | 0.5 | 1 | 2 | 5 | 12.5 | 25 | 40 | 50 |

QC samples were prepared from pools of bacterial culture supernatant or fecal samples. Analyte concentrations for QC samples were at the endogenous level or were either diluted or fortified with analytes, as necessary, so that analyte concentrations were within the calibration range for the given sample type. QC samples were stored at −80° C.

IV. General Methods

A. Sample Preparation

Bacterial Culture Supernatant Samples

Sample preparation was carried out in a polypropylene 96-well plate. Experimental samples, QC samples, and calibration standards were thawed on ice and vortexed; 50.0 μL of bacterial culture supernatant followed by 20.0 μL of the Working Internal Standard Solution (WIS) was added to the appropriate wells of the 96-well plate. For Blank-IS Samples, 50.0 μL of water and 20.0 82 L of WIS was added to appropriate wells; 70.0 μL of water was added for Blank Samples.

Solid Samples (Feces and Tissue)

Approximately 100 mg of frozen feces or tissue (Experimental Samples) was weighed into a 2 mL cryovial, and the exact weight was recorded. For Blank and Blank-IS Samples, 100 μL of water was added to 2 mL cryovials. For Calibration Standards, 100 μL of corresponding Calibration Solutions was added 2 mL cryovials. For QC Samples, 250 μL of QC Sample Extract was added to a 2 mL cryovial. A 20.0 μL volume of the WIS solution was added to Calibration Standard, Blank-IS, QC Samples, and Experimental Samples, and 20.0 μL of water was added to the blank samples.

Liquid Samples (Plasma, Serum, Urine, Saliva, and Breast Milk)

50.0 μl of Experimental Sample was added to a well of a microtiter plate. For Blank and Blank-IS Samples, 50.0 μL of water was added to a well of a microtiter plate. For Calibration Standards, 50.0 μL of corresponding Calibration Solutions was added to a well of a microtiter plate. For QC Samples, 50.0 μL of QC Sample for the corresponding sample type was added to a well of a microtiter plate. A 20.0 μL volume of the WIS solution was added to Calibration Standard, Blank-IS, QC Samples, and Experimental Samples, and 20.0 μL of water was added to the blank samples.

B. Extraction

To precipitate proteins and extract analytes, 200 μL of methanol was added to samples, and samples were shaken or vortexed for at least 1 minute, and centrifuged for 3 minutes at 3000 rpm. A 40.0 μL volume of cleared supernatant was transferred into a fresh 96-well plate, and analytical samples were derivatized. Plates were capped, vortexed, and centrifuged for 0.5 minutes at 3000 rpm. The plate was heated for 30 min at 40° C. and centrifuged for 0.5 minutes at 3000 rpm. 50.0 μL from each well was transferred into a fresh 96-well plate, and 450 μL Methanol/Water Solution (1:1) was added to all wells. Plates were capped and vortexed prior to LC-MS/MS analysis.

C. Derivatization

Figure 2:
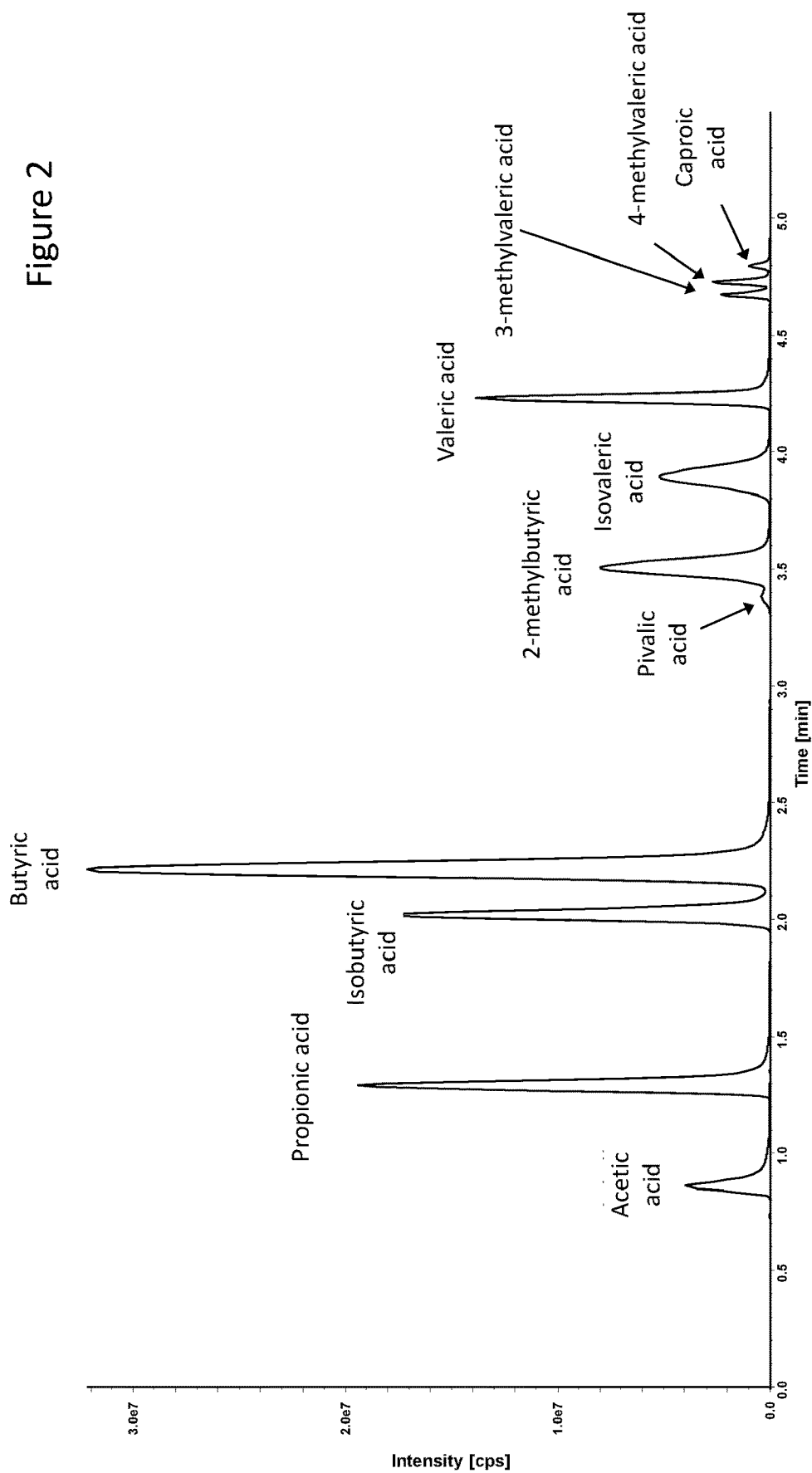
FIG. 2 shows an example chromatogram of Acetic acid (C2), Propionic acid (C3), Isobutyric acid (C4), Butyric acid (C4), Pivalic acid, 2-Methyl-butyric acid (C5), Isovaleric acid (C5), Valeric acid (C5), 3-Methylvaleric acid, 4-Methylvaleric acid, and Caproic acid (Hexanoic acid, C6), in a single chromatogram, generated from the analysis of calibration standard samples using Derivatization Procedure 2 and the LC-MS methods described herein.

The derivatization reagents 3-Nitrophenylhydrazine, 3-Chlorophenylhydrazine Hydrochloride, 2,4-Cichlorophenylhydrazine and 2,4-Difluorophenyl Hydrazine Hydrochloride were tested, and the derivatization reagents 2,4-Difluorophenyl Hydrazine Hydrochloride was and 3-Nitrophenylhydrazine Hydrochloride were selected for use in the methods described herein. The reagents 3-Nitrophenylhydrazine, 3-Chlorophenylhydrazine, and 2,4-Dichlorophenylhydrazine did not separate the C5 isomers and resulted in the co-elution of the SCFA 2-methylbutyric acid with Pivalic acid. FIG. 1 shows that Pivalic acid co-elutes with 2-Methylbutyric acid using the derivatization reagent 3-Nitrophenylhydrazine and LC-MS/MS conditions as described in Han et al. In addition to chromatographic separation, selective measurement of 2-Methylbutyric acid in the presence of Pivalic acid was achieved by using the daughter ion of m/z 125 for the 2,4-Difluorophenyl Hydrazine derivative, as the corresponding Pivalic acid derivative did not form this daughter ion (FIG. 2).

Derivatization Procedure 1

In one example, analyte extracts were derivatized using 2,4-Difluorophenyl Hydrazine Hydrochloride as the derivatization reagent and EDC Hydrochloride as a coupling catalyst. A solution of 2,4-Difluorophenyl Hydrazine Hydrochloride (10.0 µL) and a solution of EDC Hydrochloride (20.0 µL) were added to analytical samples prior to LC-MS/MS analysis for final concentrations of 25 µg/µl each.

Derivatization Procedure 2

In another example, analyte extracts were derivatized using 2,4-Difluorophenyl Hydrazine Hydrochloride, as the derivatization reagent, 1-Hydroxybenzotriazole and DIC as coupling catalysts, and pyridine as a base. The DIC, pyridine, and solutions of 2,4-Difluorophenyl Hydrazine Hydrochloride and 1-Hydroxybenzotriazole were added to analytical samples prior to LC-MS/MS analysis. Final concentrations were 25 µg/µl each for 2,4-Difluorophenyl Hydrazine Hydrochloride and 1-Hydroxybenzotriazole; 2 µl each of 100% DIC and pyridine were added to the extract.

Derivatization Procedure 3

In another example, analyte extracts were derivatized using 3-Nitrophenylhydrazine Hydrochloride, as the derivatization reagent, 1-Hydroxybenzotriazole and DIC as coupling catalysts, and pyridine as a base. The DIC, pyridine, and solutions of 3-Nitrophenylhydrazine Hydrochloride and 1-Hydroxybenzotriazole were added to analytical samples prior to LC-MS/MS analysis. Final concentrations were 25 µg/µl each for 3-Nitrophenylhydrazine Hydrochloride and 1-Hydroxybenzotriazole; 2 µl each of 100% DIC and pyridine were added to the extract.

Example 1

Measuring SCFA and Energy Metabolites

Chromatography Method

A liquid chromatography method was developed for the purification and separation in the same injection of one or more, two or more, and up to all twenty analytes selected from the group consisting of Acetic acid (C2), Propionic acid (C3), Isobutyric acid (C4), Butyric acid (C4), 2-Methylbutyric acid (C5), Isovaleric acid (C5), Valeric acid (C5), 3-Methylvaleric acid, 4-Methylvaleric acid (Isocaproic acid), Caproic acid (Hexanoic acid, C6), Pivalic acid, Lactic acid, Pyruvic acid, Fumaric acid, Succinic acid, Malic acid, alpha-Ketoglutaric acid, Aconitic acid, Citric acid, Isocitric acid, and combinations thereof. An Agilent 1290 Infinity UHPLC system equipped with a binary solvent pump unit, a refrigerated autosampler (set at 18° C.), and a column heater (set at 60° C.) was used for liquid chromatography with a reversed phase column (Waters ACQUITY C18 BEH Shield, 1.7 µm, 2.1×100 mm). Mobile phase A was 0.01% formic acid in water and mobile phase B was 0.01% formic acid in acetonitrile. Linear gradient elution, was carried out with an initial condition of 20% mobile phase B (80% mobile phase A) and 800 µL/min flow rate. The total run time, including chromatography and mass spectrometry, was 5.40 min.

Figure 3:
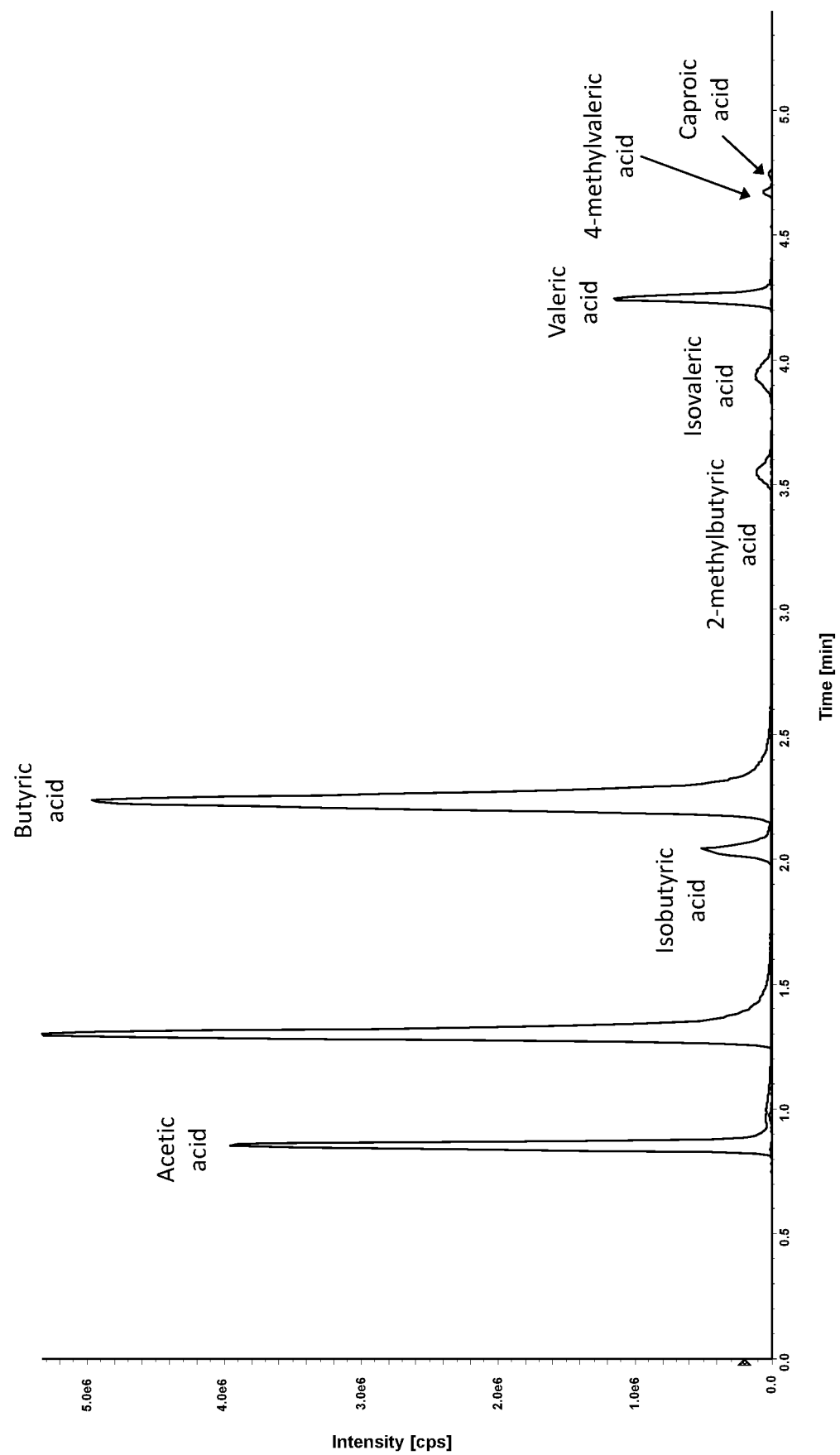
FIG. 3 shows an example chromatogram of Acetic acid (C2), Propionic acid (C3), Isobutyric acid (C4), Butyric acid (C4), 2-Methyl-butyric acid (C5), Isovaleric acid (C5), Valeric acid (C5), 4-methylvaleric acid, and Caproic acid (Hexanoic acid, C6), in a single chromatogram, generated from the analysis of fecal samples using Derivatization Procedure 2 and the LC-MS methods described herein.
Figure 4:
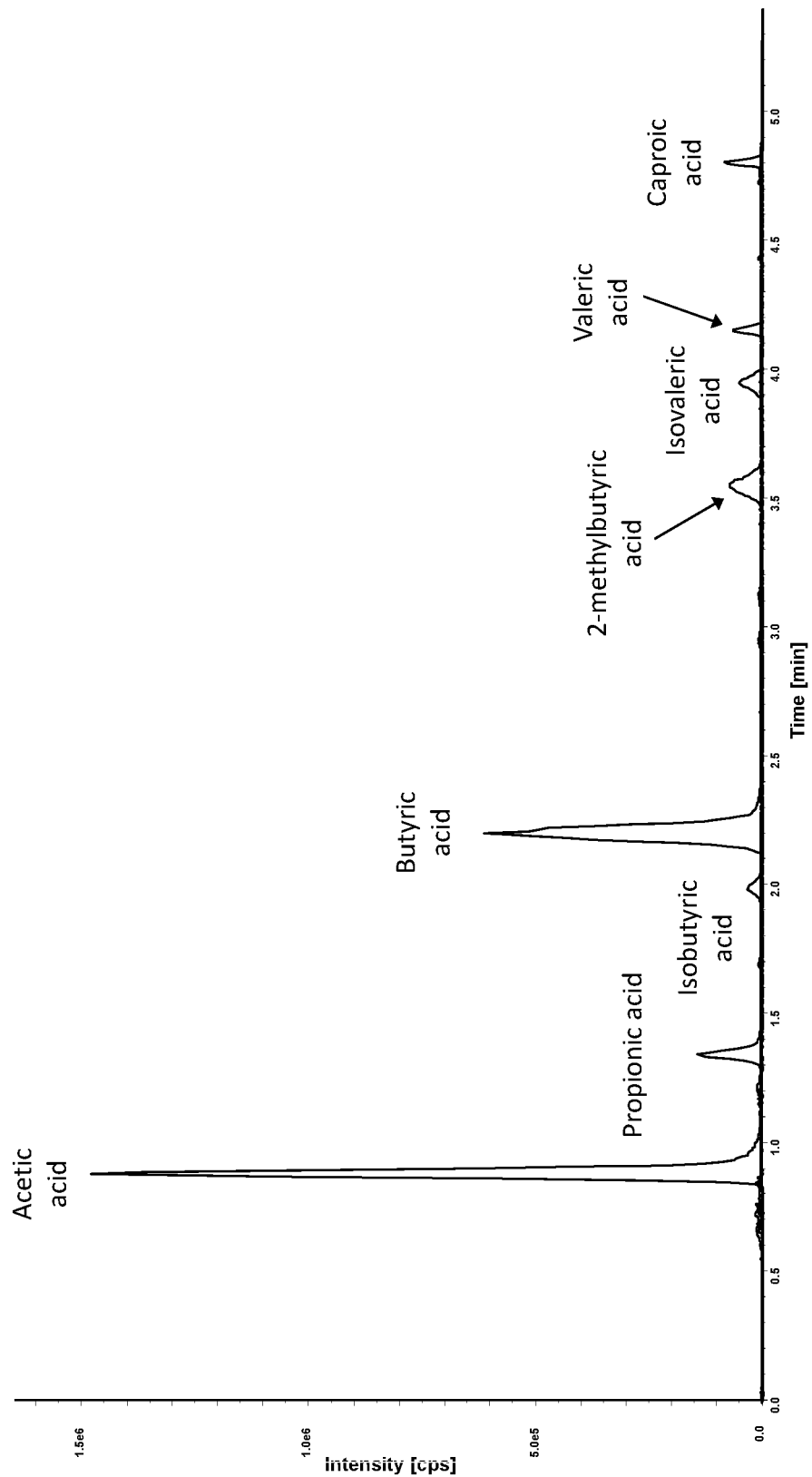
FIG. 4 shows an example chromatogram of Acetic acid (C2), Propionic acid (C3), Isobutyric acid (C4), Butyric acid (C4), 2-Methyl-butyric acid (C5), Isovaleric acid (C5), Valeric acid (C5), and Caproic acid (Hexanoic acid, C6), in a single chromatogram, generated from the analysis of bacterial culture supernatant samples using Derivatization Procedure 2 and the LC-MS methods described herein.

In one example, eighteen human fecal samples, and eighteen bacterial culture supernatant samples were prepared and derivatized according to Derivatization Procedure 2. A single fixed aliquot of 0.5 µL of the final derivatized analytical sample was injected onto the chromatography column for each sample analyzed. The chromatography method separated the ten SCFA analytes and Pivalic acid with good peak shapes and without interference from Pivalic acid. Exemplary chromatograms of the resulting separated analytes (Acetic acid (C2), Propionic acid (C3), Isobutyric acid (C4), Butyric acid (C4), 2-Methyl-butyric acid (C5), Isovaleric acid (C5), Valeric acid (C5), Isocaproate, 3-Methylvaleric acid, 4-Methylvaleric acid (Isocaproic acid), Caproic acid (Hexanoic acid, C6), and Pivalic acid) are shown in FIG. 2 for calibration standards. Approximate retention times (in minutes) were 0.9, 1.3, 2.0, 2.2, 3.4, 3.5, 3.9, 4.2, 4.65, 4.75, and 4.8 for Acetic acid (C2), Propionic acid (C3), Isobutyric acid (C4), Butyric acid (C4), Pivalic acid, 2-Methyl-butyric acid (C5), Isovaleric acid (C5), Valeric acid (C5), 3-Methylvaleric acid, 4-Methylvaleric acid (Isocaproic acid), and Caproic acid (Hexanoic acid, C6), respectively. FIGS. 3 & 4 show exemplary chromatograms for fecal and bacterial culture supernatant samples, respectively.

Figure 5A:
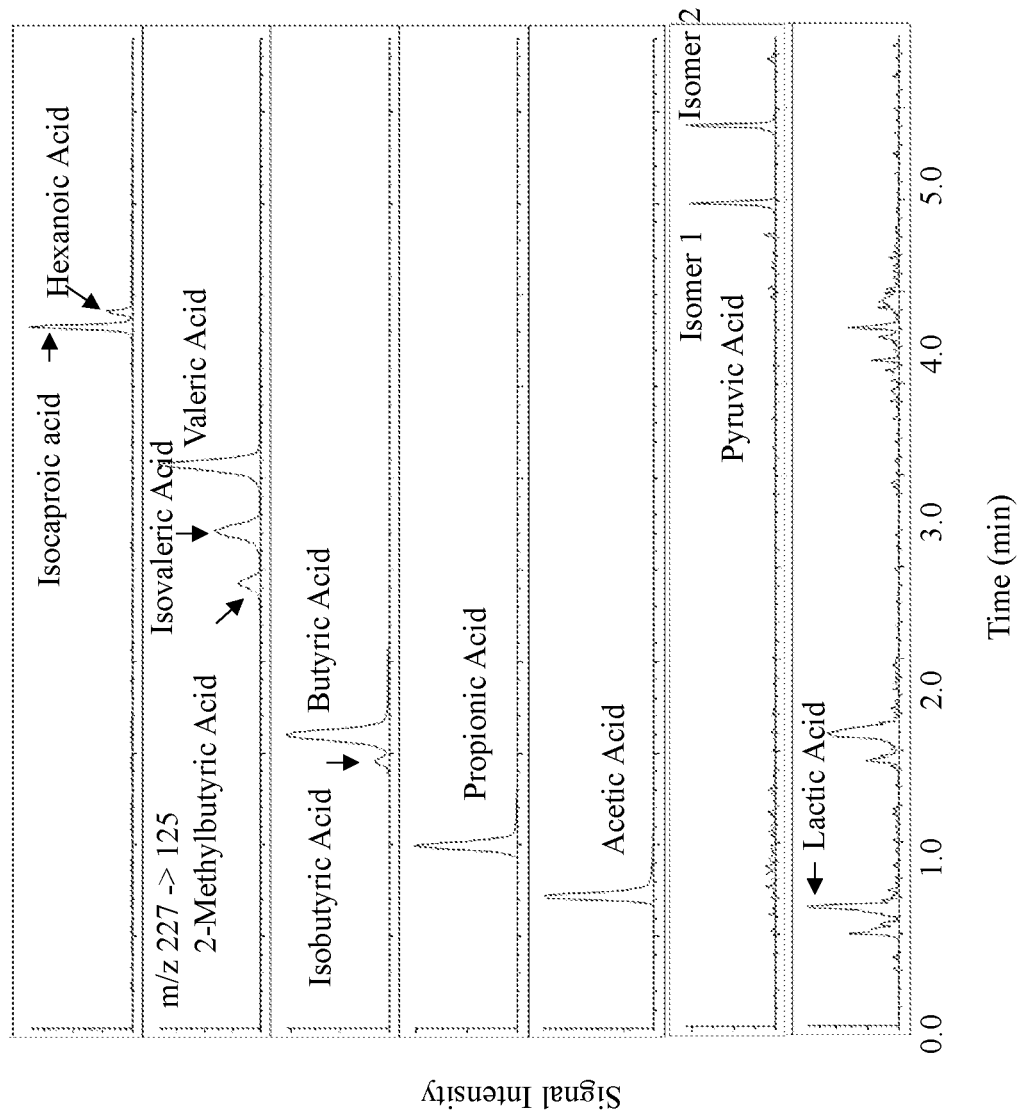
FIG. 5 (A-B) shows an example chromatogram of Acetic acid (C2), Propionic acid (C3), Isobutyric acid (C4), Butyric acid (C4), 2-Methyl-butyric acid (C5), Isovaleric acid (C5), Valeric acid (C5), Caproic acid (Hexanoic acid, C6), 4-Methylvaleric acid (Isocaproic acid), Lactic acid, Pyruvic acid, Fumaric acid, Succinic acid, Malic acid, alpha-Ketoglutaric acid, Aconitic acid, Citric acid, and Isocitric acid, from a single chromatography run, generated from the analysis of fecal samples using Derivatization Procedure 2 and the LC-MS methods described herein.
Figure 5B:
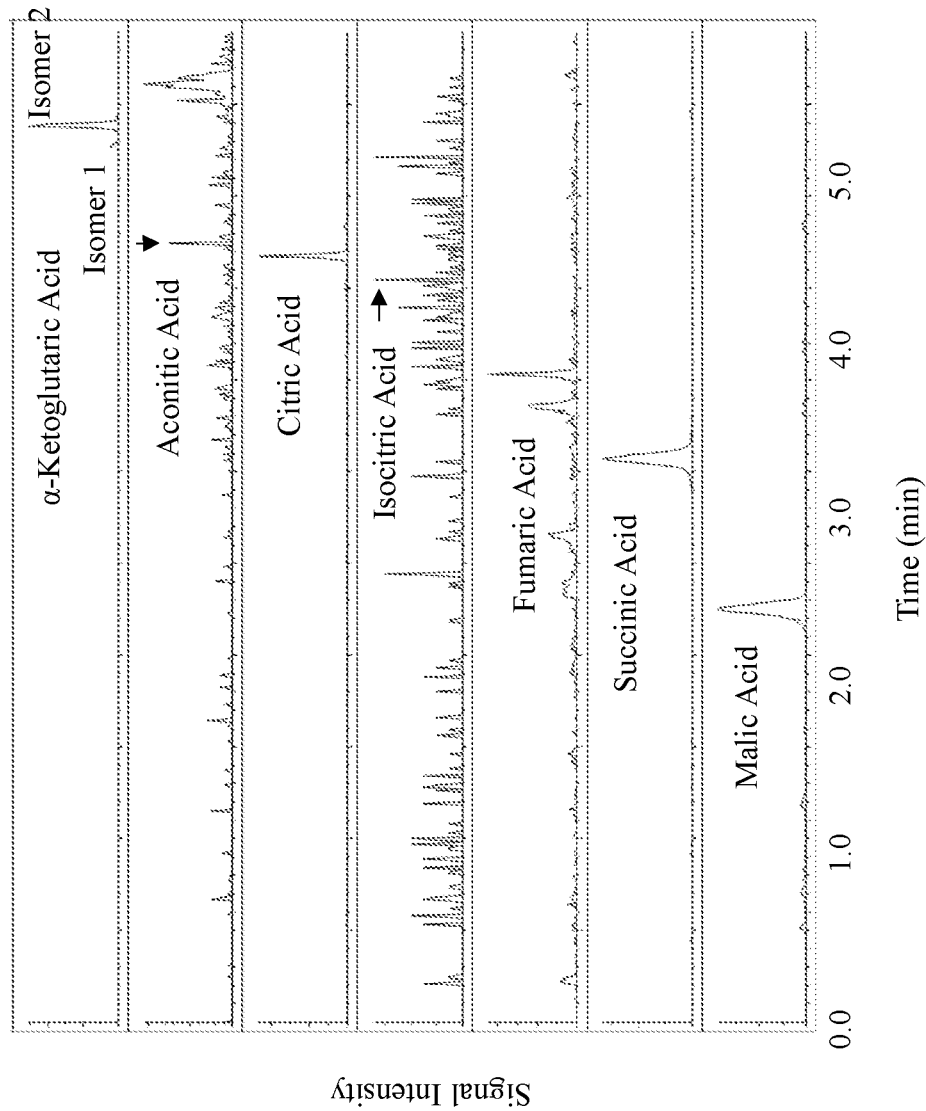

In another example, for human fecal samples prepared and derivatized according to Derivatization Procedure 2, the chromatography method separated the analytes Acetic acid (C2), Propionic acid (C3), Isobutyric acid (C4), Butyric acid (C4), 2-Methyl-butyric acid (C5), Isovaleric acid (C5), Valeric acid (C5), 4-Methylvaleric acid (Isocaproic acid), Caproic acid (Hexanoic acid, C6), Lactic acid, Pyruvic acid, Fumaric acid, Succinic acid, Malic acid, alpha-Ketoglutaric acid, Aconitic acid, Citric acid, and Isocitric acid with good peak shapes. Exemplary chromatograms of the resulting separated analytes are shown in FIG. 5A-B. A single fixed aliquot of 0.5 µL of the final derivatized analytical sample was injected onto the chromatography column for each sample analyzed. Approximate retention times (in minutes) are shown in Table 4.

Figure 6A:
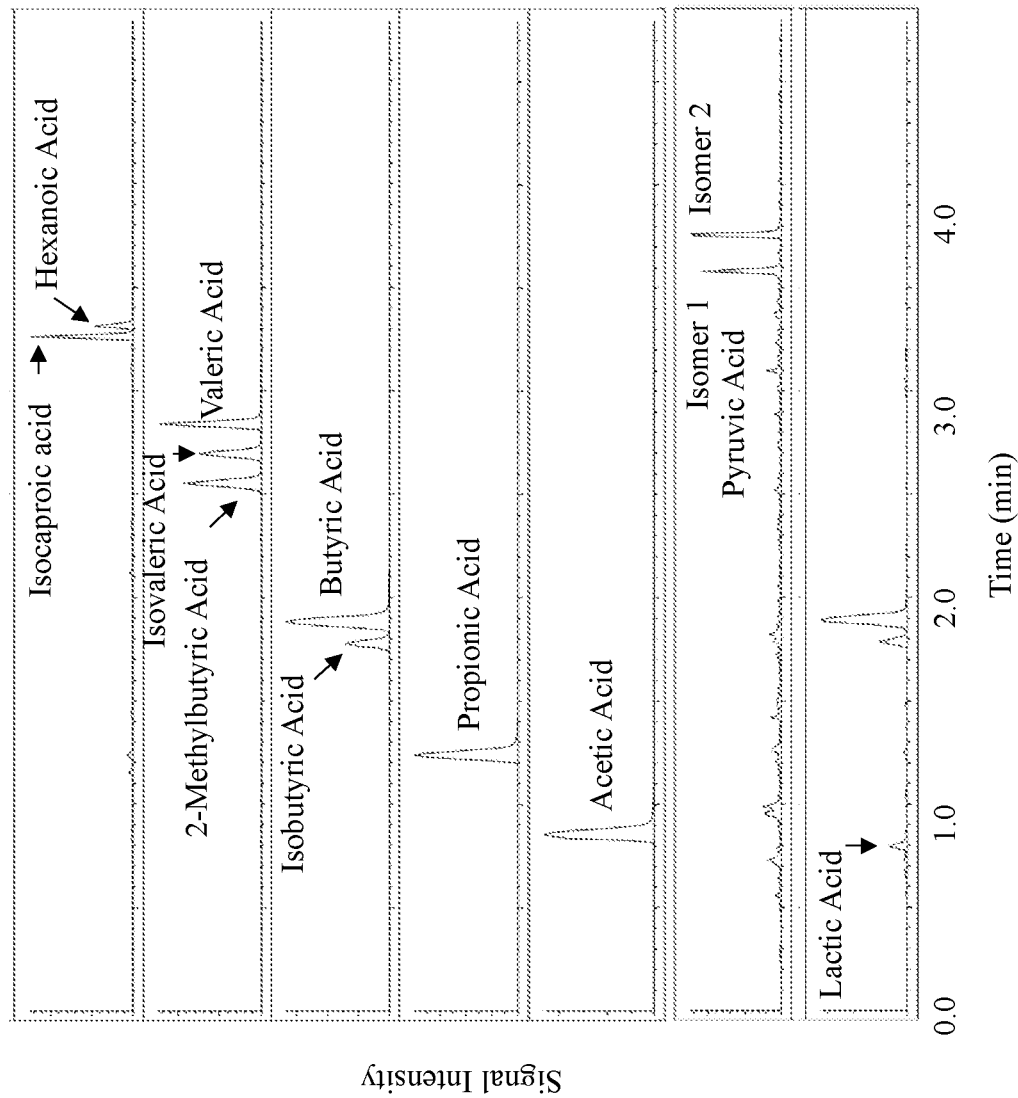
FIG. 6 (A-B) shows an example chromatogram of Acetic acid (C2), Propionic acid (C3), Isobutyric acid (C4), Butyric acid (C4), 2-Methyl-butyric acid (C5), Isovaleric acid (C5), Valeric acid (C5), Caproic acid (Hexanoic acid, C6), 4-Methylvaleric acid (Isocaproic acid), Lactic acid, Pyruvic acid, Fumaric acid, Succinic acid, Malic acid, alpha-Ketoglutaric acid, Aconitic acid, Citric acid, and Isocitric acid, from a single chromatography run, generated from the analysis of fecal samples using Derivatization Procedure 3 and the LC-MS methods described herein.
Figure 6B:
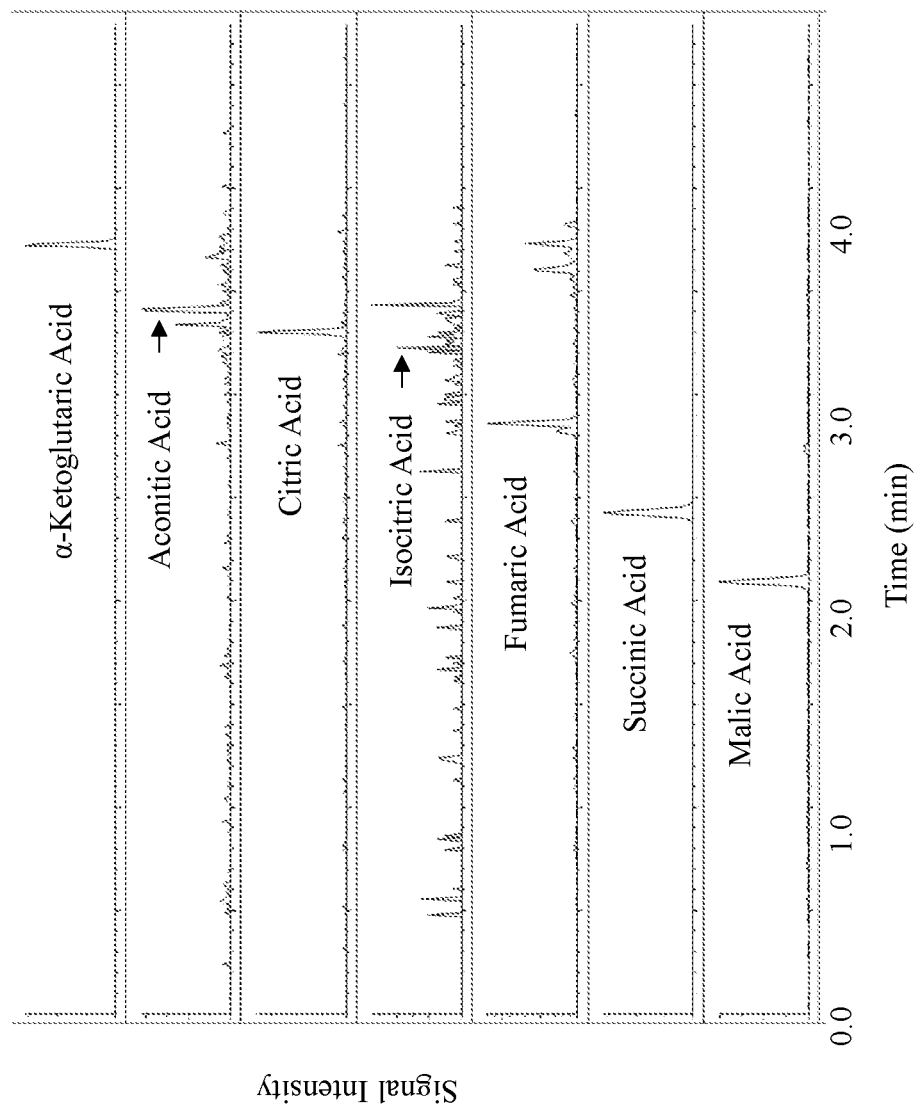

In yet another example, for human fecal samples prepared and derivatized according to Derivatization Procedure 3, the chromatography method separated the analytes Acetic acid (C2), Propionic acid (C3), Isobutyric acid (C4), Butyric acid (C4), 2-Methyl-butyric acid (C5), Isovaleric acid (C5), Valeric acid (C5), 4-Methylvaleric acid (Isocaproic acid), Caproic acid (Hexanoic acid, C6), Lactic acid, Pyruvic acid, Fumaric acid, Succinic acid, Malic acid, alpha-Ketoglutaric acid, Aconitic acid, Citric acid, and Isocitric acid with good peak shapes. Exemplary chromatograms of the resulting separated analytes are shown in FIG. 6A-B. A single fixed aliquot of 0.5 µL of the final derivatized analytical sample was injected onto the chromatography column for each sample analyzed. Approximate retention times (in minutes) are shown in Table 5.

Figure 7A:
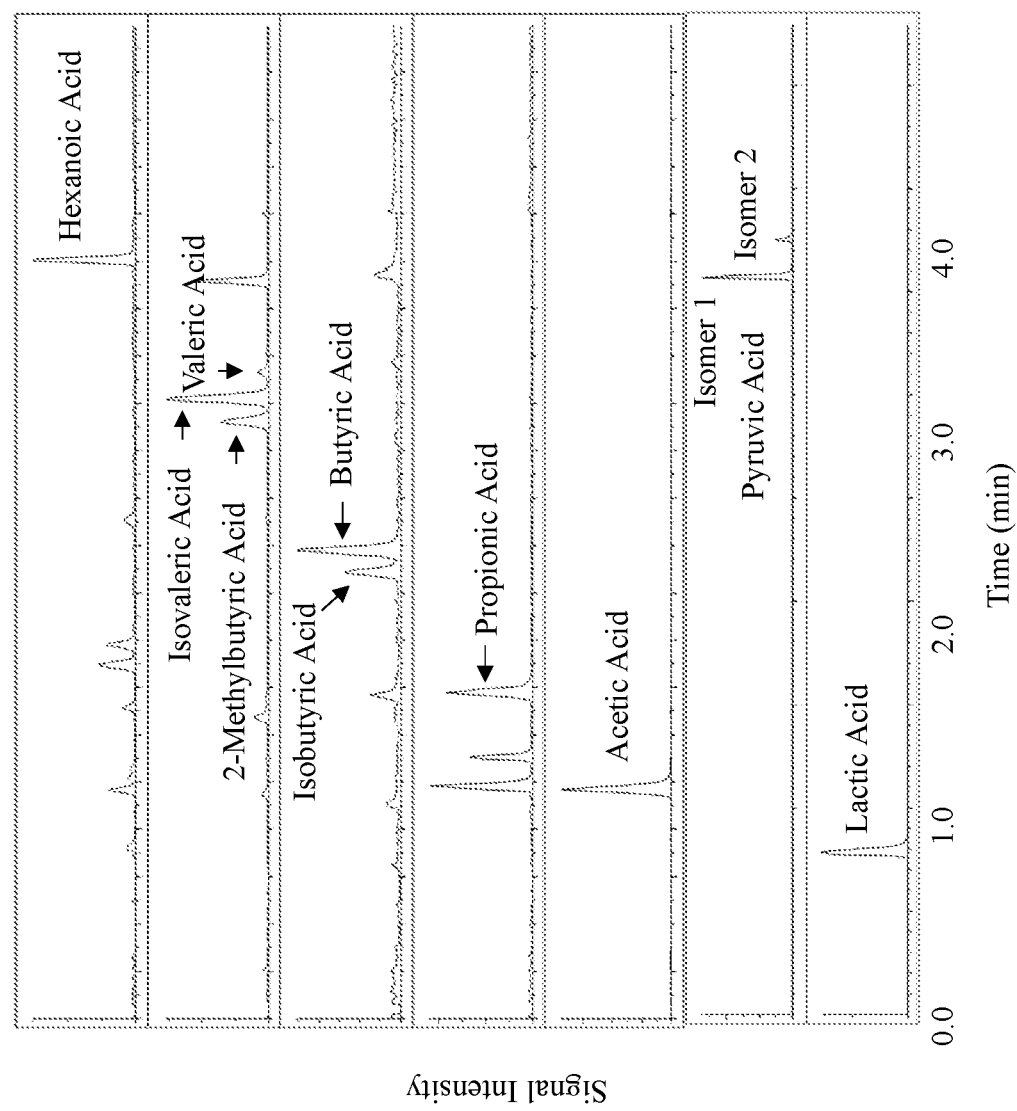
FIG. 7 (A-B) shows an example chromatogram of Acetic acid (C2), Propionic acid (C3), Isobutyric acid (C4), Butyric acid (C4), 2-Methyl-butyric acid (C5), Isovaleric acid (C5), Valeric acid (C5), Caproic acid (Hexanoic acid, C6), 4-Methylvaleric acid (Isocaproic acid), Lactic acid, Pyruvic acid, Fumaric acid, Succinic acid, Malic acid, alpha-Ketoglutaric acid, Aconitic acid, Citric acid, and Isocitric acid, from a single chromatography run, generated from the analysis of plasma samples using Derivatization Procedure 3 and the LC-MS methods described herein.
Figure 7B:
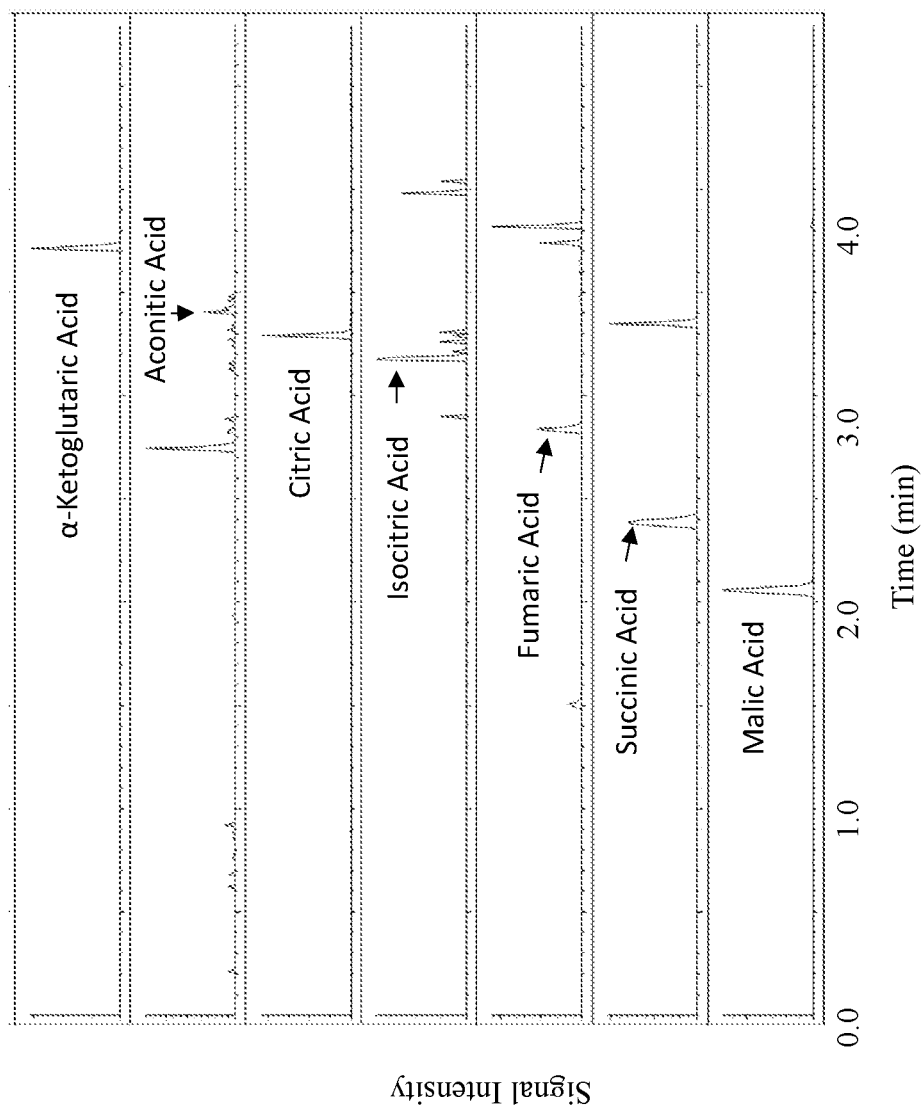

In yet another example, for human plasma samples prepared and derivatized according to Derivatization Procedure 3, the chromatography method separated the analytes Acetic acid (C2), Propionic acid (C3), Isobutyric acid (C4), Butyric acid (C4), 2-Methyl-butyric acid (C5), Isovaleric acid (C5), Valeric acid (C5), 4-Methylvaleric acid (Isocaproic acid), Caproic acid (Hexanoic acid, C6), Lactic acid, Pyruvic acid, Fumaric acid, Succinic acid, Malic acid, alpha-Ketoglutaric acid, Aconitic acid, Citric acid, and Isocitric acid with good peak shapes. Exemplary chromatograms of the resulting separated analytes are shown in FIG. 7A-B. A single fixed aliquot of 0.5 µL of the final derivatized analytical sample was injected onto the chromatography column for each sample analyzed. Approximate retention times (in minutes) are shown in Table 5.

Mass Spectrometry

The eluent from the chromatography column described in the Chromatography Method above was directly and automatically introduced into the electrospray source of a mass spectrometer. Methanol:Water (50:50) was used for needle wash. Mass spectrometry was performed on the analytical samples using an AB Sciex QTrap 5500 mass spectrometer with Turbo V source (ESI). The instrument was operated in negative multiple reaction monitoring (MRM) mode. Ionspray voltage was set at −4.5 kV, source temperature at 500° C., curtain gas (e.g., nitrogen) at 30 psi, and nebulizer and desolvation gas (e.g., nitrogen) flow rates at 70 psi, collisionally activated dissociation (CAD) gas (e.g., nitrogen) at medium.

Raw data were acquired from the instrument and processed using Analyst 1.6.2 software (AB Sciex). For quantitation, peak area ratios of analyte to internal standard were fitted against the concentrations of the calibration standards by weighted ($1/x^2$) linear least squares regression. The resulting slope and intercept of the calibration curve were used to calculate the unknown concentrations in experimental samples. Exemplary ions that were generated for the quantitation of Acetic acid (C2), Propionic acid (C3), Isobutyric acid (C4), Butyric acid (C4), 2-Methyl-butyric acid (C5), Isovaleric acid (C5), Valeric acid (C5), Caproic acid (Hexanoic acid, C6), Lactic acid, Pyruvic acid, Fumaric acid, Succinic acid, Malic acid, alpha-Ketoglutaric acid, Aconitic acid, Citric acid, and Isocitric acid when samples were derivatized using Derivatization Procedure 2 or Derivatization Procedure 3 are listed in Tables 4 and 5, respectively. The parent ions are listed under the column headed "Parent ion (m/z)", and the daughter ions used for quantitation in this example are listed in the column labeled "Daughter ion for quantitation (m/z)". The choice of daughter ion for quantitation in this example was optimized for sensitivity across the analytical measurement range; however, additional daughter ions may be selected to replace or augment the daughter ions used for quantitation in the examples.

TABLE 4

Parent and Daughter Ion Mass to Charge Ratios (m/z) of Analytes Derivatized Using Derivatization Procedure 2

| Analyte | Parent ion (m/z, ±0.5) | Daughter ion for quantitation (m/z, ±0.5) | Additional daughter ions (m/z, ±0.5) | Retention Time (min) |
|---|---|---|---|---|
| Acetic acid | 185.1 | 128.1 | 95.0; 125.1; 150.1 | 0.7 |
| Acetic acid-$d_3$ | 188.1 | 128.1 | 95.0; 125.1; 150.1 | 0.7 |
| Propionic acid | 199.1 | 125.1 | 95.0; 125.1; 150.1 | 1.0 |
| Propionic acid-$d_3$ | 202.1 | 128.1 | 95.0; 125.1; 150.1 | 1.0 |
| Isobutyric acid | 213.1 | 128.1 | 95.0; 125.1; 150.1 | 1.5 |
| Isobutyric acid-$d_3$ | 216.1 | 128.1 | 95.0; 125.1; 150.1 | 1.5 |
| Butyric acid | 213.1 | 128.1 | 95.0; 125.1; 150.1 | 1.7 |
| Butyric acid-$d_3$ | 216.1 | 128.1 | 95.0; 125.1; 150.1 | 1.7 |
| 2-Methylbutyric acid | 227.1 | 125.1 | 95.0; 128.1; 150.1 | 2.6 |
| 2-Methylbutyric acid-$d_3$ | 230.1 | 125.1 | 95.0; 128.1; 150.1 | 2.6 |
| Isovaleric acid | 227.1 | 128.1 | 95.0; 125.1; 150.1 | 2.9 |
| Isovaleric acid-$D_9$ | 236.1 | 128.1 | 95.0; 125.1; 150.1 | 2.9 |
| Valeric acid | 227.1 | 128.1 | 95.0; 125.1; 150.1 | 3.2 |
| Valeric acid-$D_3$ | 230.1 | 128.1 | 95.0; 125.1; 150.1 | 3.2 |
| Hexanoic acid | 241.1 | 128.1 | 95.0; 125.1; 150.1 | 4.0 |
| Hexanoic acid-$d_3$ | 244.1 | 128.1 | 95.0; 125.1; 150.1 | 4.0 |
| Lactic acid | 215.1 | 128.1 | 95.0; 113.1; 123.1; 143.1; 151.1; 150.1 | 0.7 |
| Lactic acid-$d_4$ | 218.1 | 128.1 | — | 0.7 |
| Pyruvic acid | 339.1 | 194.1 | 113.1; 128.1; 141.1; 150.1; 169.1; 191.1 | 4.5 (isomer1); 4.9 (isomer2) |
| Pyruvic acid-$^{13}C_3$ | 342.1 | 128.1 | 113.1 | |
| Fumaric acid | 367.1 | 219.1 | 113.1; 128.1; 162.1; 182.1; 202.1; 222.1; 225.1 | 4.5 (isomer1); 4.9 (isomer2) |
| Fumaric acid-$^{13}C_4$ | 371.1 | 128.1 | 113.1 | 4.5 (isomer1); 4.9 (isomer2) |
| Succinic acid | 369.1 | 225.1 | 113.1; 128.1; 162.1; 182.1; 205.1; 221.1 | 3.2 |
| Succinic acid-$d_4$ | 373.1 | 229.1 | — | 3.2 |
| Malic acid | 385.1 | 199.1 | 128.1; 141.1; 169.1; 179.1; 213.1; 225.1 | 2.4 |
| Malic acid-$d_3$ | 388.1 | 128.1 | — | 2.4 |
| α-Ketoglutaric acid | 523.2 | 353.2 | 113.1; 169.1; 224.1; 252.1; 265.1 | 4.8 (isomer1); 4.9 (isomer2) |
| α-Ketoglutaric acid-$^{13}C_4$ | 537.2 | 356.2 | — | 4.8 (isomer1); 4.9 (isomer2 |
| Aconitic acid | 551.2 | 409.2 | 237.1; 280.1; 365.1 | 4.3 |
| Citric acid | 569.2 | 383.2 | 169.1; 213.1; 237.1; 407.1 | 4.2 |
| Citric acid-$d_4$ | 573.2 | 384.2 | — | 4.2 |
| Isocitric acid | 569.2 | 369.1 | 199.1; 237.1; 270.1; 407.1 | 4.1 |

TABLE 5

Parent and Daughter Ion Mass to Charge Ratios (m/z) of Analytes Derivatized Using Derivatization Procedure 3

| Analyte | Parent ion (m/z, ±0.5) | Daughter ion for quantitation (m/z, ±0.5) | Additional Daughter ions (m/z, ±0.5) | Retention Time (min) |
|---|---|---|---|---|
| Acetic acid | 194.1 | 137.1 | 92.1; 106.1; 122.1; 152.1 | 0.9 |
| Acetic acid-$d_3$ | 197.1 | 137.1 | 122.1; 152.1 | 0.9 |
| Propionic acid | 208.1 | 165.1 | 152.1 | 1.3 |
| Propionic acid-$d_3$ | 213.1 | 137.1 | 152.1 | 1.3 |
| Isobutyric acid | 222.12 | 137.1 | 152.1 | 1.8 |
| Isobutyric acid-$d_3$ | 225.11 | 137.1 | 152.1 | 1.8 |
| Butyric acid | 222.11 | 137.1 | 152.1 | 1.9 |
| Butyric acid-$d_3$ | 225.1 | 137.1 | 152.1 | 1.9 |
| 2-Methylbutyric acid | 236.1 | 137.1 | 152.1 | 2.6 |
| 2-Methylbutyric acid-$d_3$ | 239.11 | 137.1 | 152.1 | 2.6 |
| Isovaleric acid | 236.1 | 137.1 | 152.1 | 2.7 |
| Isovaleric acid-$D_9$ | 245.1 | 137.1 | 152.1 | 2.7 |
| Valeric acid | 236.1 | 137.1 | 152.1 | 2.9 |
| Valeric acid-$D_3$ | 239.1 | 137.1 | 152.1 | 2.9 |
| Hexanoic acid | 250.1 | 137.1 | 152.1 | 3.3 |
| Hexanoic acid-$d_3$ | 253.1 | 137.1 | 152.1 | 3.3 |
| Lactic acid | 224.1 | 137.1 | 106.1; 122.1; 152.1 | 0.8 |
| Lactic acid-$d_4$ | 228.1 | 137.1 | 106.1; 122.1; 152.1 | 0.8 |
| Pyruvic acid | 357.2 | 178.1 | 106.1; 122.1; 150.1; 204.1 | 3.6 (isomer1); 3.8 (isomer2) |
| Pyruvic acid-$^{13}C_3$ | 360.2 | 180.1 | — | 3.3 (isomer1); 3.4 (isomer2) |
| Fumaric acid | 385.1 | 232.1 | 122.1; 150.1; 178.1; 191.1; 233.1 | 2.8 |
| Fumaric acid-$^{13}C_4$ | 389.1 | 236.1 | 179.1 | 2.8 |
| Succinic acid | 387.1 | 234.1 | 152.1; 191.1 | 2.4 |
| Succinic acid-$d_4$ | 391.1 | 238.1 | — | 2.4 |
| Malic acid | 403.1 | 208.2 | 137.1; 178.1; 222.1 | 2.1 |
| Malic acid-$d_3$ | 403.1 | 137.1 | 250.1 | 2.1 |
| α-Ketoglutaric acid | 550.2 | 371.1 | 397.1 | 3.7 |
| α-Ketoglutaric acid-$^{13}C_4$ | 554.2 | 374.1 | — | 3.7 |
| Aconitic acid | 578.2 | 425.2 | 178.1 | 3.3 (isomer1); 3.4 (isomer2) |
| Citric acid | 596.2 | 401.2 | 425.2 | 3.3 |
| Citric acid-$d_4$ | 600.2 | 402.2 | — | 3.3 |
| Isocitric acid | 596.2 | 387.2 | — | 3.2 |

Example 2

Measurement of SCFA Analytes in Experimental Samples

SCFA were measured in a sample using the methods described in Example 1 using Derivatization Method 2. The method was used to determine the absolute amount of the SCFA analytes Acetic acid (C2), Propionic acid (C3), Isobutyric acid (C4), Butyric acid (C4), 2-Methyl-butyric acid (C5), Isovaleric acid (C5), Valeric acid (C5), Caproic acid (Hexanoic acid, C6) in a variety of sample types including plasma, serum, urine, feces, breast milk, saliva, and bacterial culture supernatant.

In one example, the 8 SCFA analytes were measured in 59 plasma samples. The results of a representative sample are presented in Table 6.

In another example, the 8 SCFA analytes were measured in 120 serum samples. The results of a representative sample are presented in Table 6.

In another example, the 8 SCFA analytes were measured in 50 urine samples. The results of a representative sample are presented in Table 6.

In another example, the 8 SCFA analytes were measured in 197 fecal samples. The results of a representative sample are presented in Table 6.

In another example, the 8 SCFA analytes were measured in 140 breast milk samples. The results of a representative sample are presented in Table 6.

In another example, the 8 SCFA analytes were measured in 52 saliva samples. The results of a representative sample are presented in Table 6.

In another example, the 8 SCFA analytes were measured in 102 bacterial culture supernatant samples. The results of a representative sample are presented in Table 6.

TABLE 6

Results from Representative Samples.

| Sample Type | Acetic acid | Propionic acid | Isobutyric acid | Butyric acid | 2-Methyl butyric acid | Isovaleric acid | Valeric acid | Hexanoic acid |
|---|---|---|---|---|---|---|---|---|
| Plasma (ng/ml) | 2130 | 48.4 | 20.7 | 105 | 49.3 | 10.9 | 10.6 | 55.3 |
| Serum (ng/ml) | 6980 | 198 | 352 | 31.6 | 206 | 88.5 | 19.4 | 57 |
| Saliva (ng/ml) | 299000 | 2270 | 230 | 101 | 153 | 39.6 | 27 | 38.1 |
| Breast Milk (ng/ml) | 1750 | 170 | 33.9 | 10200 | 32.6 | 14 | 410 | 16000 |
| Urine (ng/ml) | 3280 | 110 | 94.1 | 23.7 | 288 | 34.2 | 16.6 | 148 |
| Feces (µg/ml) | 1690 | 785 | 87.8 | 795 | 63.1 | 78.4 | 131 | 3.21 |
| Bacterial Cultures (µg/ml) | 347 | 11.2 | 5.11 | 296 | 1.18 | 2.12 | 2.13 | 0.965 |

What is claimed:

1. A method for determining in a sample, by mass spectrometry, the presence, absence, or amount of two or more analytes selected from the group consisting of Acetic acid (C2), Propionic acid (C3), Butyric acid (C4), Isobutyric acid (C4), 2-Methyl-butyric acid (C5), Isovaleric acid (C5), Valeric acid (C5), Caproic acid (Hexanoic acid, C6), 3-Methylvaleric acid, 4-Methylvaleric acid (Isocaproic acid), Lactic acid, Pyruvic acid, Fumaric acid, Succinic acid, Malic acid, alpha-Ketoglutaric acid, Aconitic acid, Citric acid, Isocitric acid, and combinations thereof, wherein one of the two or more analytes is selected from the group consisting of: Acetic acid (C2), Propionic acid (C3), Butyric acid (C4), Isobutyric acid (C4), 2-Methyl-butyric acid (C5), Isovaleric acid (C5), Valeric acid (C5), Caproic acid (Hexanoic acid, C6), 3-Methylvaleric acid, 4-Methylvaleric acid (Isocaproic acid); and a different one of the two or more analytes is selected from the group consisting of Lactic acid, Pyruvic acid, Fumaric acid, Succinic acid, Malic acid, alpha-Ketoglutaric acid, Aconitic acid, Citric acid, Isocitric acid, wherein the run time is less than six minutes, the method comprising:
   a) subjecting the sample to an ionization source under conditions suitable to produce one or more ions detectable by mass spectrometry from each of the one or more analytes, wherein the one or more analytes are derivatized prior to ionization;
   b) measuring, in a single injection, by mass spectrometry, the amount of the one or more ions from each of the one or more analytes; and
   c) using the measured amount of the one or more ions to determine the amount of each of the one or more analytes in the sample.

2. The method of claim 1, wherein pivalic acid interference is eliminated.

3. The method of claim 1, wherein the sample is derivatized using at least 2,4-Difluorophenyl Hydrazine Hydrochloride or 3-Nitrophenylhydrazine Hydrochloride.

4. The method of claim 1, wherein the mass spectrometer is operated in negative mode.

5. The method of claim 1, wherein the sample has been purified by liquid chromatography prior to being subjected to an ionization source.

6. The method of claim 1, wherein the one or more ions used to determine the amount of each of the one or more analytes are one or more ions selected from the ions in Tables 4 and 5.

7. The method of claim 1, wherein the amount of Acetic acid (C2), Propionic acid (C3), and Butyric acid (C4) is determined.

8. The method of claim 1, wherein the amount Acetic acid (C2), Propionic acid (C3), Butyric acid (C4) and lactic acid is determined.

9. The method of claim 1, wherein the amount Acetic acid (C2), Propionic acid (C3), Isobutyric acid (C4), and Butyric acid (C4) is determined.

10. The method of claim 1, wherein the amount Acetic acid (C2), Propionic acid (C3), Isobutyric acid (C4), Butyric acid (C4), 2-Methyl-butyric acid (C5), Isovaleric acid (C5), Valeric acid (C5), and Caproic acid (Hexanoic acid, C6), is determined.

11. A method for determining in a sample, by mass spectrometry, the presence, absence, or amount of one or more analytes selected from the group consisting of Acetic acid (C2), Propionic acid (C3), Butyric acid (C4), Isobutyric acid (C4), 2-Methyl-butyric acid (C5), Isovaleric acid (C5), Valeric acid (C5), Caproic acid (Hexanoic acid, C6), 3-Methylvaleric acid, 4-Methylvaleric acid (Isocaproic acid), and combinations thereof, wherein the run time is less than six minutes, the method comprising:
   a) subjecting the sample to chromatographic separation [prior to being subjected to an ionization source];
   b) subjecting the sample to an ionization source under conditions suitable to produce one or more ions detectable by mass spectrometry from each of the one or more analytes, wherein the one or more analytes are derivatized using at least 2,4-Difluorophenyl Hydrazine Hydrochloride prior to ionization;
   c) measuring, in a single injection, by mass spectrometry, the amount of the one or more ions from each of the one or more analytes; and
   d) using the measured amount of the one or more ions to determine the amount of each of the one or more analytes in the sample.

12. The method of claim 11, wherein the chromatographic separation is performed using liquid chromatography and wherein the liquid chromatography is selected from the group consisting of high-performance liquid chromatography, ultra high performance liquid chromatography, and turbulent flow liquid chromatography.

13. The method of claim 11, wherein pivalic acid interference is eliminated.

14. The method of claim 11, wherein the sample is also derivatized using 3-Nitrophenylhydrazine Hydrochloride.

15. The method of claim 11, wherein the mass spectrometer is operated in negative mode.

16. The method of claim 11, wherein the one or more ions used to determine the amount of each of the one or more analytes are one or more ions selected from the ions in Tables 4 and 5.

17. A kit comprising two or more isotopically labeled analogues as internal standards for each of two or more analytes selected from the group consisting of Acetic acid (C2), Propionic acid (C3), Isobutyric acid (C4), Butyric acid (C4), 2-Methyl-butyric acid (C5), Isovaleric acid (C5), Valeric acid (C5), Caproic acid (Hexanoic acid, C6), Lactic acid, Pyruvic acid, Fumaric acid, Succinic acid, Malic acid, alpha-Ketoglutaric acid, Aconitic acid, Citric acid, Isocitric acid, and combinations thereof, wherein one of the two or more isotopically labeled analogues is for an analyte selected from the group consisting of: Acetic acid (C2), Propionic acid (C3), Butyric acid (C4), Isobutyric acid (C4), 2-Methyl-butyric acid (C5), Isovaleric acid (C5), Valeric acid (C5), Caproic acid (Hexanoic acid, C6), 3-Methylvaleric acid, 4-Methylvaleric acid (Isocaproic acid); and a different one of the two or more isotopically labeled analogues is for an analyte selected from the group consisting of Lactic acid, Pyruvic acid, Fumaric acid, Succinic acid, Malic acid, alpha-Ketoglutaric acid, Aconitic acid, Citric acid, Isocitric acid, and packaging material and instructions for using the kit.

18. The kit of claim 17 further comprising derivatization reagents, catalyst reagents, calibration standards, or quality control samples.

* * * * *